US008034571B1

(12) United States Patent
Handfield et al.

(10) Patent No.: US 8,034,571 B1
(45) Date of Patent: *Oct. 11, 2011

(54) MICROBIAL POLYNUCLEOTIDES EXPRESSED DURING INFECTION OF A HOST

(75) Inventors: Martin Handfield, Gainesville, FL (US); Ann Progulske-Fox, Keystone Heights, FL (US); L. Jeannine Brady, Gainesville, FL (US); Jeffrey D. Hillman, Gainesville, FL (US)

(73) Assignee: Oragenics, Inc., Alachua, FL (US)

(*) Notice: Subject to any disclaimer, the term of this patent is extended or adjusted under 35 U.S.C. 154(b) by 2774 days.

This patent is subject to a terminal disclaimer.

(21) Appl. No.: 09/980,845

(22) PCT Filed: Aug. 4, 2000

(86) PCT No.: PCT/US00/21340
§ 371 (c)(1),
(2), (4) Date: Apr. 8, 2002

(87) PCT Pub. No.: WO01/11081
PCT Pub. Date: Feb. 15, 2001

Related U.S. Application Data

(60) Provisional application No. 60/147,551, filed on Aug. 6, 1999.

(51) Int. Cl.
*G01N 33/53* (2006.01)
*C40B 20/08* (2006.01)
*C40B 30/04* (2006.01)
(52) U.S. Cl. .................. 435/7.1; 506/6; 506/9
(58) Field of Classification Search .............. 435/7.1; 506/6, 9
See application file for complete search history.

(56) References Cited

U.S. PATENT DOCUMENTS

| 5,789,157 | A | * | 8/1998 | Jensen et al. | 435/6 |
| 6,013,443 | A | * | 1/2000 | Heilig et al. | 435/6 |
| 6,048,527 | A | | 4/2000 | Granoff et al. | |
| 6,376,474 | B1 | * | 4/2002 | Heilig et al. | 514/44 R |
| 2004/0247611 | A1 | | 12/2004 | Bargatze et al. | |

FOREIGN PATENT DOCUMENTS

| WO | 9830910 | | 7/1998 |
| WO | WO 98/30910 | * | 7/1998 |
| WO | 9846738 | | 10/1998 |
| WO | 9905293 | | 2/1999 |
| WO | WO 99/15897 | * | 4/1999 |
| WO | 9932633 | | 7/1999 |
| WO | WO 01/11081 | | 2/2001 |

OTHER PUBLICATIONS

Ebersole et al., 1983, Human immune Responses to Oral Microorganisms, Journal of Clinical Immunology, 3(4): 321-331.*
Suk et al., Borrelia burgdorferi genes selectively expressed in the infected host, PNAS, 92: 4269-4273, 1995.*
Sharma et al., Vaccination against periodontitis: the saga continues, Expert Rev. Vaccines, 6(4): 579-590, 2007.*
Ramjeet et al., *Actinobacillus pleuropneumoniae* vaccines: from bacterins to new insights into vaccination strategies, Animal Health Research Reviews, 9(1): 25-45, 2008.*
Debeaupuis et al., 1995, Antigens of *Aspergillus fumigatus* expressed during infection, Can. J. Bot., 73 (suppl. 1): S1087-S1091.*
Edman et al., 1990, Characterization of an Immuno-dominant Variable Surface Antigen from Pathogenic and nonpathogenic *Entamoeba histolytica*, J. Exp. Med., 172: 879-888.*
Scala et al., May 1999, Selection of HIV-Specific Immunogenic Epitopes by Screening Random Peptide Libraries with HIV-1-Positive Sera, The Journal of immunology, 162: 6155-6161.*
Suk, et al., "Borrelia burgdorferi genes selectively expressed in the infected host", *Proc. Natl. Acad. Sci. USA*, vol. 92, pp. 4269-4273, 1995.
Handfield, et al., "Strategies for isolation of in vivo expressed genes from bacteria", *FEMS Microbiology Reviews*, 23, pp. 69-91, 1999.
PCT International Search Report for PCT/US00/21340.
PCT International Search Report for PCT/US03/06768, mailed Aug. 13, 2003.
Suk et al., *Borrelia burgdorferi* genes selectively expressed in the infected host. Proc. Natl. Acad. Sci. USA May 1995, vol. 95:4269-4273.
Lai et al. Identification of genes induced in vivo during *Klebsiella pneumoniae* CG43 infection. Infection and Immunity. Nov. 2001. vol. 69 (11), p. 7140-7145.
Ebersole, et al., "An ELISA for Measuring Serum Antibodies to *Actinobacillus actinomycetemcomitans*", *Journal of Periodontal Research*, vol. 15, pp. 621-632, 1980.
Tsai, et al., "Serum Neutralizing Activity Against *Actinobacillus actinomycetemcomitans* Leukotoxin in Juvenile Periodontitis", *Journal of Clinical Periodontology*, vol. 8, pp. 338-348, 1981.
Slots, et al., "Selective Medium for Isolation of *Actinobacillus actinomycetemcomitans*", *Journal of Clinical Microbiology*, vol. 15, No. 4, pp. 606-609, 1982.
Ebersole, et al., "Human Immune Responses to Oral Microorganisms. II. Serum Antibody Responses to Antigens from *Actinobacillus actinomycetemcomitans* and the Correlation with Localized Juvenile Periodontitis", *Journal of Clinical Immunology*, vol. 3, No. 4, pp. 321-331, 1983.
Brady, et al., "Two Novel Antigens Associated with Group B *Streptococci* Identified by a Rapid Two-Stage Radioimmunoassay", *The Journal of Infectious Diseases*, vol. 158, No. 5, pp. 965-972, 1988.

(Continued)

*Primary Examiner* — Amber D. Steele
(74) *Attorney, Agent, or Firm* — McDonnel Boehnen Hulbert & Berghoff LLP

(57) ABSTRACT

Disclosed are methods for obtaining antigens that are expressed by pathogenic microorganism during an infection process, as well as the antigens so obtained. Also disclosed are isolated polynucleotides encoding said antigens, recombinant polypeptides expressed from the isolated polypeptides, antibodies capable of forming immune complexes with the obtained antigens, and various other compositions useful in the detection, diagnosis, prevention and/or treatment of a microbial infection. The methods of the invention utilize pooled sera from patients who have partly or completely undergone infection by a microbial organism in order to obtain genes that are expressed during in vivo but not during in vitro growth of the microbial organism.

22 Claims, 7 Drawing Sheets

OTHER PUBLICATIONS

Chanyangam, et al., "Contribution of a 28-Kilodalton Membrane Protein to the Virulence of *Haemophilus influenzae*", *Infection and immunity*, vol. 59, No. 2, pp. 600-608, 1991.

Mekalanos, "Environmental Signals Controlling Expression of Virulence Determinants in Bacteria", *Journal of Bacteriology*, vol. 174, No. 1, pp. 1-7, 1992.

Mahan, et al., "Selection of Bacterial Virulence Genes that are Specifically Induced in Host Tissues", *Science*, vol. 259, pp. 686-688, 1993.

Li, et al., "A New Gene Involved in Stationary-Phase Survival Located at 59 Minutes on the *Escherichia coli* Chormosome", *Journal of Bacteriology*, vol. 176, No. 19, pp. 6015-6022, 1994.

Fleischmann, et al., "Whole-Genome Random Sequencing and Assembly of *Haemophilus influenzae* Rd", *Science*, vol. 269, pp. 496-512, 1995.

Haubek, et al., "Highly Toxic Clone of *Actinobacillus actinomycetemcomitans* in Geographically Widespread Cases of Juvenile Periodontitis in Adolescents of African Origin", *Journal of Clinical Microbiology*, vol. 34, No. 6, pp. 1576-1578, 1996.

Valdivia, et al., "Fluorescence-Based Isolation of Bacterial Genes Expressed within Host Cells", *Science*, vol. 277, pp. 2007-2011, 1997.

Yoshida, et al., "Identification of a Genetic Locus Essential for Serotype b-Specific Antigen Synthesis in *Actinobacillus actinomycetemcomitans*", *Infection and Immunity*, vol. 66, No. 1, pp. 107-114, 1998.

Heithoff, et al., "Dissecting the Biology of a Pathogen During Infection", *Trends Microbiology*, vol. 5, pp. 509-513, 1997.

Smith, "What happens to Bacterial Pathogens in vivo?", *Trends in Microbiology*, vol. 6, No. 6 pp. 239-243, 1998.

Handfield, et al., "Strategies for Isolation of in vivo Expressed Genes from Bacteria", *FEMS Microbiol. Rev.*, pp. 69-91, 1999.

Chiang, et al., "In vivo Genetic Analysis of Bacterial Virulence", *Annu. Rev. Microbiol.*, vol. 53, pp. 129-54, 1999.

Slots, et al., "*Actinobacillus actinomycetemcomitans* and *Porphyromonas gingivalis* in Human Periodontal Disease: Occurrence and Treatment", *Periodontology 2000*, vol. 20, pp. 82-121, 1999.

Kinane, et al., "Humoral Immune Response to *Actinobacillus actinomycetemcomitans* and *Porphyromonas gingivalis* in Periodontal Disease", *Periodontology 2000*, vol. 20, pp. 289-340, 1999.

Hautefort, et al., "Measurement of Bacterial Gene Expression in vivo", *Phil. Trnas. R. Soc. London B*, vol. 355, pp. 601-611 2000.

Handfield, et al., "IVIAT: A Novel Method to identify Microbial Genes Expressed Specifically During Human Infections," *Trends in Microbiology*, vol. 8, No. 7, pp. 336-339 (Jul. 2000).

Rollins, et al., "In Vivo Induced Antigen Technology (IVIAT)," *Cellular Microbiology*, vol. 7, No. 1, pp. 1-9 (2005).

\* cited by examiner

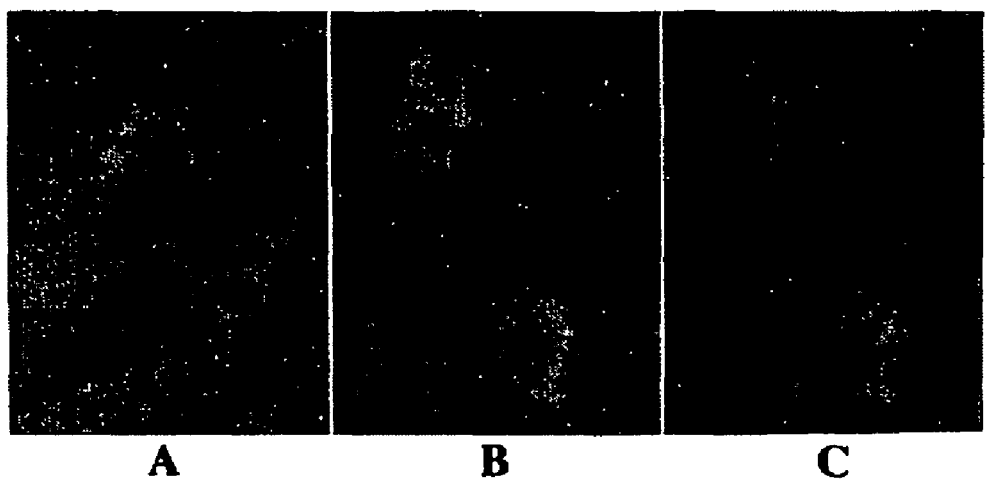
FIG. 4

Table 2. Confirmation and characterization of the IVIAT subclones.

| Subclone | Reactivity with human sera +IPTG | Strongest homology (identity at amino acid level) | Organism | Possible biological role | Reference |
|---|---|---|---|---|---|
| pET30b/ BL21(DE3) |  | N/A | N/A | N/A | |
| Aa2004 |  | HlpA (67%) | H. influenzae | Virulence associated lipoprotein | (14) |
| Aa2005 |  | Orf4 (100%) | 16. actinomycetemcomitans | Glycosyltransferase | (15) |
| Aa2008 |  | HI0701 (68%) | H. influenzae | Unknown | |
| Aa2009 |  | SurE (63%) | H. influenzae | Stress associated | (16) |
| Aa2010 |  | HI0457 (83%) | H. influenzae | Unknown | |
| Aa2011 |  | KthY (69%) | H. influenzae | Thymidylate kinase | (17) |

FIG. 6

Figure 7
Table 1. Characterization of the IVIAT open reading frames. (* Putative ribosome binding site.)
| IVIAT clone | Schematic representation of ORFs | IPTG inducibility |
|---|---|---|
| 17 | 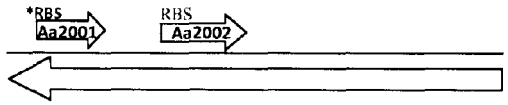 | + |
| 26 | 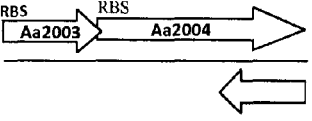 | + |
| 30 | 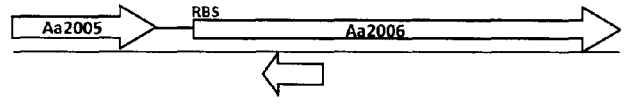 | + |
| 37 | 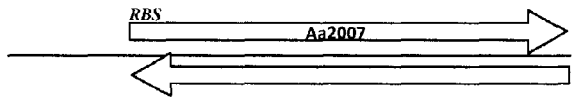 | + |
| 39.1 | 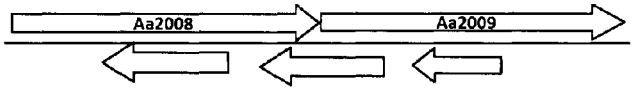 | + |
| 46-2 | 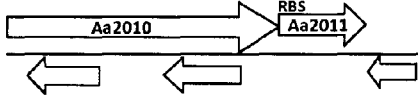 | + |
| 47-4 | 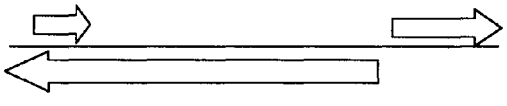 | − |
| 58-3 | 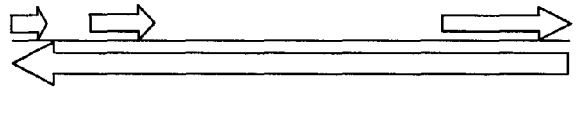 | − |

MICROBIAL POLYNUCLEOTIDES EXPRESSED DURING INFECTION OF A HOST

PRIORITY

This application is a Section 371 National Stage Application of International Application No. PCT/US00/2134, filed Aug. 4, 2000, which claims priority from provisional application 60/147,551, filed Aug. 6, 1999, which is herein incorporated by reference.

GOVERNMENT INTERESTS

This invention was made with Government support under Grant Number DE11857 awarded by the National Institute of Dental and Craniofacial Research. The Government has certain rights in the invention.

TECHNICAL AREA OF THE INVENTION

This invention provides methods and compositions for identifying and obtaining microbial polynucleotides expressed during infection of a host and the use of these polynucleotides in the diagnosis, treatment, and prevention of microbial infections.

BACKGROUND OF THE INVENTION

Microbial infections are complex, dynamic processes that evolve constantly within the host. In many instances, virulence gene expression is modulated in response to the changing environment encountered at the site of infection. Mekalanos, *J. Bacteriol.* 174:1-7 (1992); Mahan et al. *Science* 259: 686-688 (1993). It is unlikely that all regulated virulence determinants of a pathogen can be identified in vitro because it is technically impossible to determine and mimic all of the complex and changing environmental stimuli that occur at the site of an infection. Pioneering technologies such as in vivo expression technology (IVET), signature-tagged mutagenesis (STM) and differential fluorescence induction (DFI) were designed to identify genes specifically expressed in vivo, and fill the gaps in our understanding of microbial pathogenesis. Handfield & Levesque, *FEMS Microbiol. Rev.* 23:69-91 (1999); Heithoff et al., *Trends Microbiol.* 5:509-513 (1997); Chiang et al., *Ann. Rev. Microbiol.* 53:129-154 (1999); Hautefort & Hinton, *Phil. Trans. R. Soc. London Ser. B*, 255:601-611 (2000). All of these methods depend on a reasonable assumption: namely, that genes which are specifically induced during in vivo growth are likely to be important to the pathogenic process.

Although remarkably powerful, all of these technologies have certain limitations. Their major drawback is that they depend on the use of animal models of infection; animal models are not available for many pathogens and, in those cases where an animal model is available, it might not closely approximate the human condition. Consequently, a number of examples exist in the literature of erroneous conclusions being drawn by extrapolation of results from animal models to human infections. Smith, *Trends Microbiol.* 6:239-243 (1998). Further, many of these schemes are not readily applicable to genetically "undomesticated" microbes, that is microbes for which there is no well established or reliable means for genetic manipulation. Additionally, IVET, STM, and related technologies are technically difficult, and therefore restrict analysis to a single representative strain of the microbe and to only one or several time points in the infection process.

An example of a microbe that is not easily characterized by IVET, STM, and related technologies is *Actinobacillus actinomycetemcomitans* (Aa), an etiologic agent of periodontal diseases. Aa has emerged as one of the best examples of a bacterium demonstrating a direct correlation with disease manifestation in the oral cavity. Act is known to be the etiologic agent for localized juvenile periodontitis (LJP). See, Slots & Ting, *Periodontol.* 2000, 20:82-121 (1999). Despite the fact that some Aa virulence factors have been identified, other important contributors to the infectious process have yet to be identified.

SUMMARY OF THE INVENTION

It is an object of the invention to provide methods for identifying polynucleotides useful for vaccine design, diagnostics, and antibiotherapy. It is a further object of the invention to provide methods and compositions useful in vaccine design, diagnosis, and therapy of *A. actinomycetemcomitans* infection. This and other objects of the invention are provided by one or more of the embodiments described below.

The invention provides methods useful for identifying polynucleotides expressed by a microbe during infection of a host. One embodiment provides a method of identifying a polynucleotide of a microbe that is expressed in vivo. Antibodies against antigens that are expressed by the microbe in vivo and in vitro are adsorbed with cells or cellular extracts of the microbe that have been grown in vitro. Unadsorbed antibodies are isolated and are probed against an expression library of the microbe's DNA or RNA. A polynucleotide of the microbe that is expressed in vivo is isolated and identified.

Another embodiment of the invention provides a method of comparing polynucleotides of a microbe that are expressed in vivo at different stages of infection of the microbe. A first sera sample from one or more hosts infected with or previously infected with the microbe is adsorbed with cells or cellular extracts of the microbe that have been grown in vitro. Each host is in about the same stage of the infection. A second sera sample from one or more hosts infected with or previously infected with the microbe is adsorbed with cells or cellular extracts of the microbe that have been grown in vitro. Each host is in about the same stage of the infection and the stage of the infection is different from the stage of infection in the first sample. Unadsorbed antibodies from the first serum sample and from the second serum sample are isolated. A first expression library of the microbe is probed with the unadsorbed antibodies from the first serum sample, and a second expression library is probed with the unadsorbed antibodies from the second serum sample. The first and second expression libraries can be the same expression library. Polynucleotides of the microbe that are expressed in vivo are identified for the first and second serum sample. The polynucleotides of the microbe that are expressed in vivo at different stages of infection of the microbe are compared.

Still another embodiment of the invention provides a method of comparing polynucleotides of a microbe that are expressed in vivo, wherein the microbe has infected its host by different routes of infection. A first sera sample from one or more hosts infected with or previously infected with the microbe is adsorbed with cells or cellular extracts of the microbe that have been grown in vitro. Each host has been infected by about the same route of infection. A second sera sample from one or more hosts infected with or previously infected with the microbe are adsorbed with cells or cellular extracts of the microbe that have been grown in vitro. Each host has been infected by about the same route of infection, and the route of infection is different from the route of infection for the first sample. Unadsorbed antibodies are isolated from the first serum sample and from the second serum sample. A first expression library of the microbe is probed with the unadsorbed antibodies from the first serum sample, and a second expression library is probed with the unadsorbed antibodies from the second serum sample. The first and second expression libraries can be the same expression library. The polynucleotides of the microbe that are expressed in vivo are identified for the first and second serum sample and the polynucleotides of the microbe that are expressed in vivo by different routes of infection of the microbe are compared.

Another embodiment of the invention provides a method of confirming an animal model of microbial infection as a valid model. A first sera sample from one or more animal model hosts infected with or previously infected with a microbe, is adsorbed with cells or cellular extracts of the microbe that have been grown in vitro. A second sera sample from one or more second hosts infected with or previously infected with the microbe, is adsorbed with cells or cellular extracts of the microbe that have been grown in vitro, where the second host is a different species of animal than the animal model host. Unadsorbed antibodies are isolated from the first serum sample and from the second serum sample. A first expression library of the microbe is probed with the unadsorbed antibodies from the first serum sample, and a second expression library is probed with the unadsorbed antibodies from the second serum sample. The first and second expression libraries can be the same expression libraries. Polynucleotides of the microbe that are expressed in vivo are identified for the first and second serum sample and polynucleotides of the microbe that are expressed in vivo in the animal model host and the second host are compared. If the polynucleotides expressed in vivo in the animal model and in the second host are the same or similar, then the animal model is confirmed as a valid model.

Yet another embodiment of the invention provides a purified polypeptide comprising at least 5 contiguous amino acids of an amino acid sequence selected from the group consisting of SEQ ID NO:10, SEQ ID NO:12, SEQ ID NO:14, SEQ ID NO:16, SEQ ID NO:18, and SEQ ID NO:20.

Even another embodiment of the invention provides a purified polypeptide comprising an amino acid sequence selected from the group consisting of SEQ ID NO:10, SEQ ID NO:12, SEQ ID NO:14, SEQ ID NO:16, SEQ ID NO:18, and SEQ ID NO:20.

Another embodiment of the invention provides a purified polynucleotide comprising at least about 15 contiguous nucleic acids of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:13, SEQ ID NO:15, SEQ ID NO:17, and SEQ ID NO:19.

Yet another embodiment of the invention provides a purified polynucleotide comprising a sequence selected from the group consisting SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ TD NO:13, SEQ ID NO:15, SEQ ID NO:17, and SEQ ID NO:19.

Another embodiment of the invention provides a method for identifying the presence of a first polynucleotide. A sample suspected of containing the first polynucleotide is contacted with a second polynucleotide comprising at least about 15 nucleotides of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:13, SEQ ID NO:15, SEQ ID NO:17, and SEQ ID NO:19, under hybridization conditions. The presence of a hybridized first and second polynucleotide complex is detected and the presence of the first polynucleotide is identified.

Still another embodiment of the invention provides a method of eliciting an immune response. A purified polypeptide comprising at least about 5 contiguous amino acids of an amino acid sequence selected from the group consisting of SEQ ID NO:10, SEQ ID NO:12, SEQ ID NO: 14, SEQ ID NO:16, SEQ ID NO:18, and SEQ ID NO:20 is administered to an animal. An immune response is elicited.

Even another embodiment of the invention provides a method of treating, preventing, or ameliorating a disease or infection caused by *A. actinomycetemcomitans*. A purified polypeptide comprising at least about 5 contiguous amino acids of an amino acid sequence selected from the group consisting of SEQ ID NO:10, SEQ ID NO:12, SEQ ID NO:14, SEQ ID NO:16, SEQ ID NO:18, and SEQ ID NO:20 is administered to an animal. The disease or infection is treated, prevented, or ameliorated.

The invention thus provides methods for identifying antigens expressed during an actual microbial infection that do not rely on animal models. The methods can be used with microbes for which there is no well established or reliable means for genetic manipulation and allow for the analysis of a pool of strains of a microbe that represent all of the various clinically important clonotypes. The methods of the invention further provide a technique of defining a timeline for antigen production by the microbe throughout the course of a natural infection process. The staging of individual in vivo induced antigens provides relevant information on the pathogenesis of the microorganism and on the host response to the infection. This in turn provides valuable insights for rationale vaccine design, diagnostics, and antibiotherapy.

The combination of screening, confirmation, and staging methods of the invention to identify and test in vivo induced antigens is far superior to existing in vivo expression technologies by virtue of its efficiency and direct assessment in natural human infections. The methods are rapid and simple, which renders the screening of a whole genome possible in a timely fashion.

The invention further provides for the first time methods for a comprehensive analysis of the expression of infection-related antigens at the genomic level of different clinical strains of a microbe and of different stages of infection in the host.

Additionally, polynucleotides isolated by the methods of the invention can advantageously be studied by conventional techniques, including mutant analysis in animal models, with the confidence that the polynucleotide is actually expressed in infections, which is not the case with other available technologies.

BRIEF DESCRIPTION OF THE DRAWINGS

FIG. 4 shows specific in vivo induction of Aa2008. Plaque samples were thawed on ice, homogenized by brief vortexing at 4° C., and immediately heat-fixed on microscope slides. Plaque samples and matched in vitro grown *A. actinomycetemcomitans* isolates taken from selective medium (Slots, *Clin. Microbiol.* 15:606 (1982)) were probed in parallel with FITC-labeled monospecific antibody directed against antigen Aa2008 and the TR-labeled *A. actinomycetemcomitans*-specific monoclonal antibody. Samples were examined by fluorescence microscopy (excitation wavelength 488 nm). Double color analysis, using matched differential emission filters, was performed to identify individual cells that were simultaneously labeled with FITC and TR. Bacterial cells in plaque that reacted with TR-labeled anti-*A. actinomycetemcomitans* monoclonal antibody (panel A) also reacted with FITC-labeled anti-Aa2008 antibody (panel B) and these signals were found to colocalize (panel C). In contrast, matched in vitro grown *A. actinomycetemcomitans* reacted with the TR-labeled anti-*A. actinomycetemcomitans* monoclonal antibody (panel D) but not with FITC-labeled anti-Aa2008 antibody (panel E) and therefore no colocalization was observed (panel F).

FIG. 6 shows Table 2, which demonstrates confirmation and characterization of the IVIAT subclones.

FIG. 7 shows Table 1, which provides a characterization of the IVIAT open reading frames. "*" is a putative ribosome binding site.

SEQUENCE LISTING

This application contains a sequence listing submitted on compact disk. The sequence listing submitted on compact disc, in compliance with 37 C.F.R. §1.52(e)(5), is incorporated herein by reference. Two separate compact discs have been submitted, each containing the file "00-505 ST25" (26,624 bytes in size), and each created on Mar. 16, 2006.

DETAILED DESCRIPTION OF THE INVENTION

Figure 1:
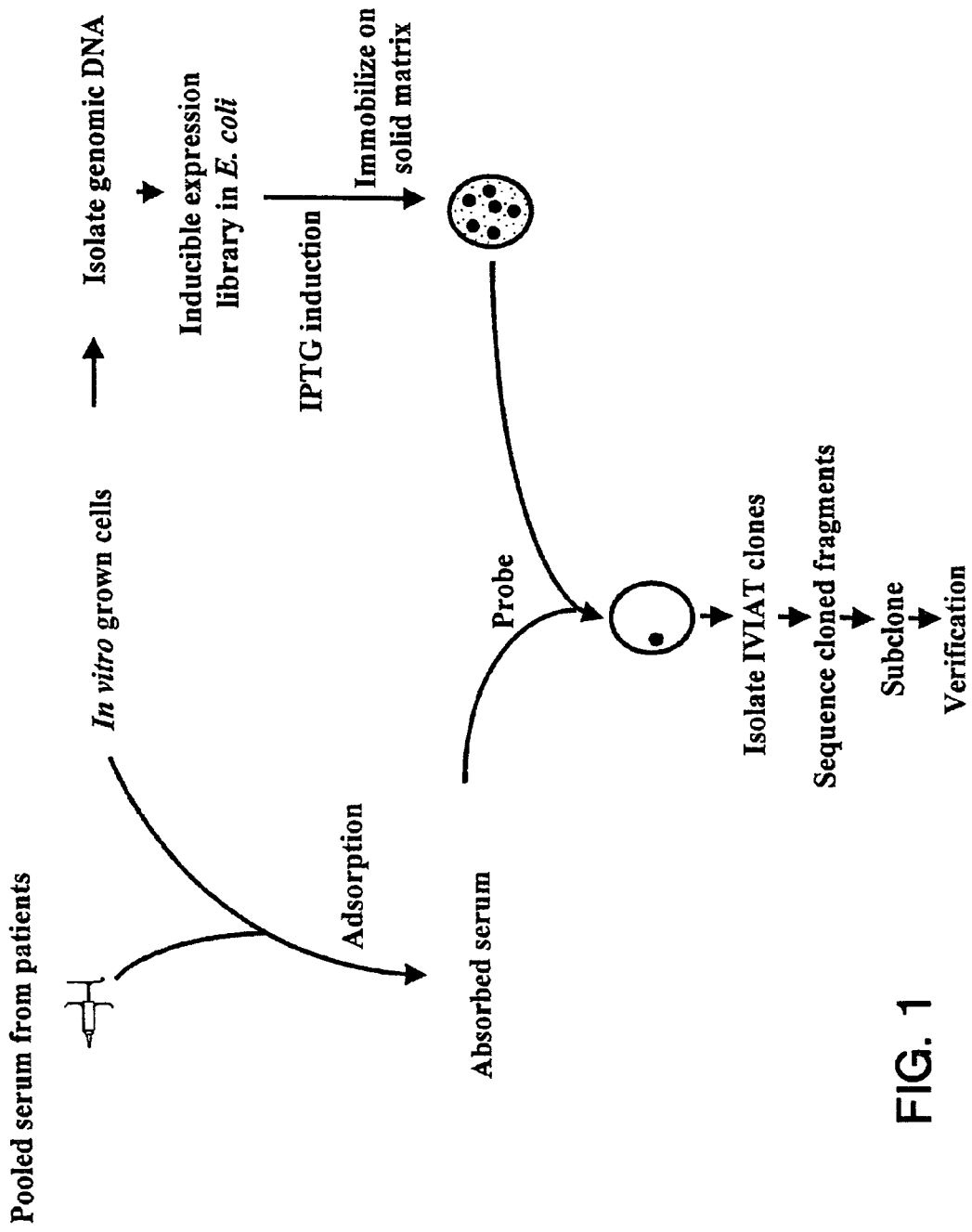
FIG. 1 shows an in vivo induced antigen technology (IVIAT) scheme. IVIAT can begin with serum from one or more patients who have or recently had the disease or infection of interest. Such sera are individually tested to verify that they exhibit measurable antibody titers versus the microbial pathogen. One or more such reactive serum samples are adsorbed with cultured cells and lysates of the pathogen to remove antibodies reactive with antigens made during in vitro growth. The resulting adsorbed serum still contains antibodies reactive with immunogenic proteins produced by the pathogen only during in vivo growth. It is used to probe an expression library of the pathogen's DNA or RNA cloned in a convenient host. Reactive clones are isolated, and the cloned insert is sequenced. If more than one open reading frame is present on an insert, each is individually subcloned and retested with the adsorbed serum to identify which one encodes the reactive antigen. For independent verification, the polynucleotide is overexpressed, and the resulting recombinant protein is purified and used to raise monospecific antibodies. The antibodies are used to probe biological samples taken from patients infected with the pathogen. Reactivity with cells of the pathogen in clinical samples, but not with cells of the pathogen grown in vitro, provides direct confirmation that the antigen is expressed only during in vivo growth.

The present invention provides methods and compositions for identifying and isolating polynucleotides that are expressed only during in vivo growth of a microbe or pathogen. Briefly, the methods, termed in vivo induced antigen technologies (IVIAT), comprise obtaining a sample of antibodies against antigens that are expressed by the microbe in vivo and in vitro and adsorbing these antibodies with cells or cellular extracts of the microbe that have been grown in vitro. An example of a sample of antibodies that can be used in the invention is sera from patients who have been or are infected with the microbe. See, e.g. FIG. 1. The unadsorbed antibodies are isolated and are used to probe an expression library of the microbe's DNA or RNA. Reactive clones can be isolated and the cloned fragments sequenced.

IVIAT Methodology

A sample of antibodies against antigens that are expressed by a microbe in vivo and in vitro is collected. The sample can comprise the serum of a host or hosts infected with or previously infected with the microbe. Because a host from which serum is collected has undergone or is actively engaged in an actual infection by the microbe of interest, the host's serum contains antibodies produced against microbial antigens expressed during the in vivo infectious process. Serum from an individual host may be used or pooled sera from two or more hosts can be used. For example, sera from about 2, 5, 25, 100, 500, or 1,000 hosts may be pooled for use in the instant invention.

The optimum number of serum samples to use depends on the type of information that is being sought. If the main interest is in targets for vaccines and diagnostics, one or several sera samples should suffice to identify those proteins that are immunogenic in most individuals. On the other hand, if the main interest is a more detailed analysis of the potential molecular mechanisms used by the pathogen, the use of a larger pool of sera would reduce the possibility of missing genes or polynucleotides of interest due to variability in the human immune response. In cases where the pathogen causes protracted disease, pooled serum from patients in early, middle and late stages of infection or sequential samples taken from patients during acute and convalescent phases of infection would offer the best chance of identifying transiently expressed in vivo induced proteins. Also, certain pathogens can infect humans by more than one route (e.g., via a wound, gastrointestinal tract, respiratory tract, or skin); in such cases, selective pooling of serum from patients infected by various routes may enable the identification of route-specific in vivo induced proteins. In cases where different clonal variants or strains of the microbe cause disease, selective pooling of scrum from patients infected by various clonal variants or strains can enable the study of the pathogenesis of each variant or strain.

A host may be any kind of animal. For example, hosts can comprise humans, baboons, chimpanzees, macaques, cattle, sheep, pigs, horses, goats, dogs, cats, rabbits, guinea pigs, rats, mice, chickens, ducks, fish, and shellfish.

The microbe or pathogen can be any kind of a bacterium, a virus, a parasite, a prion, or a fungus. For example, the microbe can be *Candida, Aspergillus, Sporothrix, Blastomyces, Histoplasma, Cryptococcus, Pneumocystis, Coccidioides, Tinea, Toxoplasma, Plasmodium, Pseudomonas, Acti-*

*nobacillus, Staphylococcus, Bacillus, Clostridium, Listeria, Corynebacterium, Actinomyces, Mycoplasma, Nocardia, Bordetella, Brucella, Francisella, Legionella, Enterobacter, Escherichia, Klebsiella, Proteus, Salmonella, Shigella, Streptococcus, Yersinia, Vibrio, Campylobacter, Helicobacter, Bacteroides, Chlamydia, Borrelia, Treponema, Leptospira, Aeromonas, Rickettsia, Ascaris, Cryptosporidium, Cyclospora, Entamoeba, Giardia, Shistosoma, Trypanosoma*, herpes virus, cytomegalovirus, Epstein-Barr virus, hepatitis virus, adenovirus, papillomavirus, polyomavirus, enterovirus, rotavirus, influenza virus, paramyxovirus, rubeola virus, rhabdovirus, human immunodeficiency virus, arenavirus, rhinovirus, and reovirus. The microbe or pathogen can also be any kind of veterinary microbe or pathogen. See e.g., Veterinary Microbiology, Hirsh & Zee, Eds., Blackwell Science, Inc., Malden, Mass., 1999; Clinical Veterinary Microbiology, Quinn, Ed., Wolfe Publishing, London, (1994).

Antibodies which bind to antigens that are produced during in vitro propagation of the microbe of interest are eliminated from the sample of antibodies against antigens that are expressed by the microbe in vivo and in vitro. The antibodies that are produced in vitro can be removed from the sample by, for example, adsorbtion. Preferably, a sample containing antibodies against antigens that are expressed by the microbe in vivo and in vitro, such as a serum sample of an infected host, are contacted with in vitro grown whole cells, cell extracts or both of the microbe, or whole cells, extracts of whole cells, or both of cells that are infected with the microbe of interest, e.g. a prokaryotic or eukaryotic cell infected with a virus or parasite.

All or substantially all of the antibodies in the antibody sample whose corresponding antigens are derived from in vitro grown microbes will bind to these antigens to form immune complexes. However, antibodies directed against antigens that are specifically expressed during the in vivo infectious process will remain uncomplexed since their corresponding antigens are not present in the in vitro grown cells and/or cell extracts. The adsorbtion step can be performed by, for example, contacting the antibody sample with whole cells and/or cell extracts that are immobilized on a solid support, such as a nitrocellulose membrane. See, Brady & Daphtary, *J. Infect. Dis.* 158:965-972 (1988). Optionally, the whole cell and/or cell extract sample can be denatured before use to expose additional immunoreactive epitopes. Several successive adsorbtions can be performed using the same or different adsorbtion methodologies.

After the adsorbtion step or steps, unbound antibodies are separated from the antibody-antigen complexes. After elimination of antibodies produced in response to microbial antigens expressed in vitro, the sample will comprise antibodies produced in response to antigens expressed in vivo. This sample can then be used to screen one or more, same or different, genomic expression libraries, for example, plasmid or bacteriophage genomic expression libraries, of the microbe of interest. Methods of constructing genomic expression libraries are well known in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989). Optionally, DNA or RNA from more than one strain or clonal variant of the microbe of interest can be pooled for expression library construction. Methods for screening these libraries with one or more labeled or unlabeled antibody-containing samples and for identifying and isolating clones from the library that encode the reactive antigens of interest are also well known in the art, e.g., colony blotting methods See, e.g., Ausubel (1994); Maniatis (1989).

Reactive clones identified by screening expression libraries of the microbe of interest can be characterized by conventional analysis. For example, the clone can be sequenced and the presence of open reading frames can be predicted, for example, using Fickett's, start/stop codon or other methods. See, e.g., Fickett, *Nucleic Acids Res.* 10:5303-5318 (1982); Solovyev, *Nucleic Acids Res.* 22:5156-5163 (1994); Saqi, *Protein Eng.* 8:1069-1073 (1995), Ladunga and Smith, *Protein Eng.* 20:101-110 (1997); Birney, *Nucleic Acids Res.* 24:2730-2739 (1996).

Identification of signal sequences, particularly likely ribosome binding sites and transcription termination sequences, can also be made since the information provided by these analysis can be helpful in prioritizing the subcloning of open reading frames if more than one is present on the cloned insert. Moreover, the obtained sequence information can be used to identify sequence similarities to known polynucleotides, e.g., by BLAST analysis, and possible relationships to proven or putative virulence factors can be evaluated. In instances where more than one open reading frame is present on a cloned insert, all of them may be analyzed for their ability to express in vivo induced antigens. For example, each open reading frame can be independently subcloned and tested with the adsorbed serum to identify in vivo induced antigens.

In vivo induced antigens identified by IVIAT can be directly verified as actually expressed by the microbe at the site of infection in the host by directly probing biological samples taken from disease sites of infected patients by any method known in the art. For example, a polypeptide which is expressed from a clone suspected of expressing an in vivo induced antigen can be used to raise polyclonal antibodies in mice. Optionally, the polynucleotide encoding the suspected antigen can be overexpressed and the resulting polypeptide purified and used to raise polyclonal antibodies. The antibodies can be labeled with, for example, fluorescein isothiocyanate (FITC). A biological sample from a disease site of a host infected with the microbe of interest is obtained. The biological sample and a matched in vitro grown sample of the microbe are assayed by, for example, immunofluorescence microscopy. The labeled antibodies will react with the microbe found in the biological sample, but will not react with in vitro grown cells. These results can provide direct evidence that the microbe expresses the IVIAT antigen exclusively during in vivo growth.

Once an antigen has been identified and confirmed as an in vivo induced antigen, the purified antigen can be used to screen the sera of individual patients for reactive antibodies. For example, a serum sample can be obtained from a patient suspected of having a particular microbial infection. The sample can be probed for reactive antibodies with a labeled, purified antigen.

For those microbes that actually have a validated animal model, the polynucleotides identified by IVIAT can also be studied by conventional techniques, including mutant analysis, with the a priori confidence that the polynucleotide is actually expressed and relevant in host infections. IVIAT can also be used to validate in vitro and animal models by identifying those that reproduce the same or similar expression pattern seen with IVIAT in humans or other animal hosts. These confirmed models can then be used for further conventional analysis of the pathogen.

Polypeptides

Polypeptides of the invention can either be full-length polypeptides or fragments of polypeptides. For example, fragments of polypeptides of the invention can comprise about 5, 10, 25, 50, 100, 200, 250, 500, 750, or 1,000 amino acids of polypeptides of the invention. Examples of polypeptides of the invention include *Actinobacillus Actinomycetemcomitans* (Aa) SEQ ID NO:10, SEQ ID NO:12, SEQ ID NO:14, SEQ ID NO:16, SEQ ID NO:18, and SEQ ID NO:20. Homologous amino acid sequences which are at least about 75, preferably about 90, 96, 98, or 99% identical to the nucleotide sequences shown in SEQ ID NO:10, SEQ ID NO:12, SEQ ID NO:14, SEQ ID NO:16, SEQ ID NO:18, and SEQ ID NO:20 are also Aa polypeptides.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Polypeptides of the invention further comprise biologically functional equivalents of at least about 5, 10, 25, 50, 100, 200, 250, or 500 amino acids of the polypeptides shown in SEQ ID NO:10, SEQ ID NO:12, SEQ ID NO:14, SEQ ID NO:16, SEQ ID NO:18, and SEQ ID NO:20. A polypeptide is a biological equivalent if it reacts about the same to a polypeptide of the invention in an assay such as an immunohistochemical assay, an ELISA, an RIA, or a western blot assay. Preferably, the assay is a competition assay wherein the biologically equivalent polypeptide is capable of reducing binding of the polypeptide of the to a corresponding reactive antigen or antibody by about 80, 95, 99, or 100%.

Polypeptides of the invention preferably comprise an antigen that is recognized by an antibody reactive against the microbe of interest. The antigen preferably comprises one or more epitopes (or antigenic determinants). An epitope can be a linear, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span the entire polypeptide sequence, can be prepared by proteolytic cleavage. By starting with, for example, 100-mer polypeptide fragments, each fragment can be tested for the presence of epitopes recognized in an enzyme-linked immunosorbent assay (ELISA). For example, in an ELISA assay a microbial polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific adsorbtion is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

Preferably, a polypeptide of the invention is produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system.

If desired, a polypeptide can be produced as a fusion protein, which can also contain other amino acid sequences, such as amino acid linkers or signal sequences, as well as ligands useful in protein purification, such as glutathione-S-transferase, histidine tag, and staphylococcal protein A. More than one polypeptide of the invention can be present in a fusion protein.

Polynucleotides

Polynucleotides of the invention contain less than an entire microbial genome and can be RNA or single- or double-stranded DNA. Preferably, the polynucleotides are purified free of other components, such as proteins and lipids. The polynucleotides of the invention encode the polypeptides described above. Polynucleotides of the invention can also comprise other nucleotide sequences, such as sequences coding for linkers, signal sequences, heterologous signal sequences, TMR stop transfer sequences, transmembrane domains, or ligands useful in protein purification such as glutathione-S-transferase, histidine tag, and staphylococcal protein A.

Degenerate nucleotide sequences encoding the polypeptides of the invention, as well as homologous nucleotide sequences which are at least about 75, preferably about 90, 96, 98, or 99% identical to the nucleotide sequences shown in SEQ ID NO:1, SEQ ID NO:2, SEQ ID NO:3, SEQ ID NO:4, SEQ TD NO:5, SEQ ID NO:6, SEQ ID NO:7, SEQ ID NO:8, SEQ ID NO:9, SEQ ID NO:11, SEQ ID NO:13, SEQ ID NO:15, SEQ TD NO:17, and SEQ ID NO:19 and the complements thereof are also polynucleotides of the invention. Percent sequence identity can be calculated as described in the "Polypeptides" section. Complementary DNA (cDNA) molecules, species homologs, and variants of Aa polynucleotides which encode biologically active Aa polypeptides also are Aa polynucleotides. Preferably, a polynucleotide of the invention comprises about 5, 10, 15, 50, 100, 500, or 1,000 nucleotides of a nucleic acid sequences shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:13, SEQ ID NO:15, SEQ ID NO:17, and SEQ ID NO:19.

Polynucleotides of the invention can be isolated from nucleic acid sequences present in, for example, a biological sample, such as plaque, saliva, sputum, blood, urine, feces, cerebrospinal fluid, amniotic fluid, wound exudate, or tissue, from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences which do not occur in nature. If desired, polynucleotides can be cloned into an expression vector comprising, for example, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

A vector comprising a polynucleotide of the invention can be transformed into, for example, bacterial, yeast, insect, or mammalian cells so that the polypeptides of the invention can be expressed in and isolated from cell culture. Any of those techniques which are available in the art can be used to introduce polynucleotides into the host cells. These include, but are not limited to, transfection with naked or encapsulated nucleic acids, cellular fusion, protoplast fusion, viral infection, and electroporation.

Polynucleotides of the invention can be used, for example, as probes or primers to detect the presence of microbial polynucleotides in a sample, such as a biological sample. The ability of such probes to specifically hybridize to microbial polynucleotide sequences will enable them to be of use in detecting the presence of complementary sequences in a given sample. Polynucleotide probes of the invention can hybridize to complementary sequences in a sample such as a biological sample, including plaque, saliva, sputum, blood, urine, feces, cerebrospinal fluid, amniotic fluid, wound exudate, or tissue. Polynucleotides from the sample can be, for example, subjected to gel electrophoresis or other size separation techniques or can be dot blotted without size separation. The polynucleotide probes are preferably labeled. Suitable labels, and methods for labeling probes are known in the art, and include, for example, radioactive labels incorporated by nick translation or by kinase, biotin, fluorescent probes, and chemiluminescent probes. The polynucleotides from the sample are then treated with the probe under hybridization conditions of suitable stringencies.

Depending on the application, varying conditions of hybridization can be used to achieve varying degrees of selectivity of the probe towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging form about 20° C. to about 55° C. The presence of a hybridized complex comprising the probe and a complementary polynucleotide from the sample indicates the presence of the microbe or polynucleotide sequence in the sample.

Methods of Eliciting an Immune Response

Polypeptides or polynucleotides of the invention can be used to elicit an immune response in a host. Elicitation of an immune response can be used, inter alia, to provide model systems to optimize immune responses to microbes and to provide prophylactic or therapeutic treatment against microbial infection. Elicitation of an immune response can also be used to treat, prevent, or ameliorate a disease or infection caused by a microbe or pathogen. An immune response includes humoral immune responses and cell mediated immune responses, or a combination thereof. Preferably, an immune response is a humoral immune response.

The generation of an antibody titer by an animal against a microbe can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to a microbe can be identified by eliciting antibodies directed against microbial polypeptides of different lengths. Antibodies elicited by a particular polypeptide epitope can then be tested using an ELISA assay to determine which polypeptides contain epitopes that are most effective at generating a strong response. Polypeptides or fusion proteins which contain these epitopes or polynucleotides encoding the epitopes can then be constructed and used to elicit a strong antibody response.

A polypeptide or a polynucleotide of the invention can be administered to an animal, such as a mouse, rabbit, guinea pig, macaque, baboon, chimpanzee, human, cow, sheep, pig, horse, dog, cat, chicken, and duck, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide is preferably delivered as "naked DNA."

Administration of a polynucleotide or a polypeptide can be by any means known in the art, including intramuscular, intradermal, intraperitoneal, or subcutaneous injection, intranasal, mucosal, topical, and oral, including injection using a biological ballistic gun ("gene gun"). Preferably, a polynucleotide or polypeptide is accompanied by a protein carrier for oral administration. A combination of administration methods may also be used to elicit an immune response.

Administration of polypeptides or polynucleotides can elicit an immune response in the animal that lasts for at least 1 week, 1 month, 3 months, 6 months, 1 year, or longer. Optionally, an immune response can be maintained in an animal by providing one or more booster injections of the polypeptide or polynucleotide at 1 month, 3 months, 6 months, 1 year, or more after the primary injection.

A composition of the invention comprising a polypeptide, polynucleotide, or a combination thereof is administered in a manner compatible with the particular composition used and in an amount which is effective to elicit an immune response as detected by, for example, an ELISA, as described above. A polynucleotide is preferably injected intramuscularly to a large mammal, such as a baboon, chimpanzee, or human, at a dose of 1 ng/kg, 10 ng/kg, 100 ng/kg, 1000 ng/kg, 0.001 mg/kg, 0.1 mg/kg, or 0.5 mg/kg. A polypeptide is preferably injected intramuscularly to a large mammal, such as a human, at a dose of 0.01, 0.05, 0.5, 0.75, 1.0, 1.5, 2.0, 2.5, 5 or 10 mg/kg. Polypeptides and/or polynucleotides can be administered either to an animal that is not infected with a microbe of interest or can be administered to a microbe-infected animal. The particular dosages polynucleotides or polypeptides in a composition will depend on many factors including, but not limited to the species, age, and general condition of the mammal to which the composition is administered, and the mode of administration of the composition. An effective amount of the composition of the invention can be readily determined using only routine experimentation. In vitro and in vivo models described herein can be employed to identify appropriate doses. If desired, co-stimulatory molecules or adjuvants can also be provided before, after, or together with the compositions.

Antibodies and their Use

Antibodies of the invention are antibody molecules that specifically and stably bind to a microbial polypeptide of the invention or fragment thereof. An antibody of the invention can be a polyclonal antibody, a monoclonal antibody, a single chain antibody (scFv), or a part of an antibody. Parts of antibodies include Fab and F(ab)$_2$ fragments. Antibodies can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering polypeptide of the invention to an animal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antibodies are known in the art.

Additionally, monoclonal antibodies directed against epitopes present on a polypeptide of the invention can also be readily produced. For example, normal B cells from a mammal, such as a mouse, immunized with polypeptide of the invention can be fused with, for example, HAT-sensitive mouse myeloma cells to produce hybridomas. Hybridomas producing microbe-specific antibodies can be identified using RIA or ELISA and isolated by cloning in semi-solid agar or by limiting dilution. Clones producing microbe-specific antibodies are isolated by another round of screening. Techniques for producing and processing monoclonal antibodies are known in the art.

Antibodies, either monoclonal and polyclonal, which are directed against microbial antigens, are particularly useful for detecting the presence of microbes or microbial antigens in a sample, such as a serum sample from a microbe-infected human. An immunoassay for a microbial antigen may utilize one antibody or several antibodies. An immunoassay for a microbial antigen may use, for example, a monoclonal antibody directed towards a microbial epitope, a combination of monoclonal antibodies directed towards epitopes of one microbial polypeptide, monoclonal antibodies directed towards epitopes of different microbial polypeptides, polyclonal antibodies directed towards the same microbial antigen, polyclonal antibodies directed towards different microbial antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate microbes or microbial antigens by immunoaffinity columns. The antibodies can be affixed to a solid support by, for example, adsorbtion or by covalent linkage so that the antibodies retain their immunoselective activity. Optionally, spacer groups may be included so that the antigen binding site of the antibody remains accessible. The immobilized antibodies can then be used to bind microbes or microbial antigens from a sample, such as a biological sample including saliva, plaque, sputum, blood, urine, feces, cerebrospinal fluid, amniotic fluid, wound exudate, or tissue. The bound microbes or microbial antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development.

Antibodies can be detected and/or quantified using for example, direct binding assays such as radioimmunoassay (RIA) or ELISA assays. Antibodies of the invention can be also be used to treat, prevent, or ameliorate a microbial infection, to diagnose or detect the presence or absence of a microbe, and to purify an antigen or antigens that the antibody specifically binds.

Compositions Comprising Polypeptides or Polynucleotides

The invention also provides compositions comprising polypeptides or polynucleotides. Compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, malodextrin, ethanol, or the like, singly or in combination, as well as substances such as wetting agents, emulsifying agents, or pH buffering agents. Liposomes can also be used as a carrier for a composition of the invention.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D- isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The compositions of the invention can be formulated into ingestable tablets, buccal tablets, troches, capsules, elixirs, suspensions, syrups, wafers, injectable formulations, mouth-washes, dentifrices, and the like. The percentage of one or more polypeptides or polynucleotides of the invention in such compositions and preparations can vary from 0.1% to 60% of the weight of the unit.

The following are provided for exemplification purposes only and are not intended to limit the scope of the invention described in broad terms above. All references cited in this disclosure are incorporated herein by reference.

EXAMPLE 1

Identification of In Vivo Induced Microbial Polypeptides from *Actinobacillus* Actinomycetemcomitans (Aa)-Injected Patients: Adsorbtion of LJP Serum To demonstrate the effectiveness of IVIAT, it was used to study in vivo gene induction of an oral pathogen, *Actinobacillus actinomycetemcomitans* (Aa) the putative etiologic agent of certain periodontal diseases, and, in particular, localized juvenile periodontitis (LJP) (Slots & Ting, *Periodontol.* 2000, 20:82-121 (1999)). Aa is well suited for this purpose since it typically evokes a strong humoral immune response in periodontitis patients (Kinane et al. *Periodontol.* 2000, 20:289 (2000)) and there is currently no reliable animal model with which to study this disease.

Serum samples were obtained from 20 periodontitis patients identified by family history and clinical and radiographic examinations. Microbiological and immunological analyses indicated a role for Aa as the etiologic agent in each of these cases. See, e.g., Ebersole et al. *J. Clin. Immunol.* 3:321 (1983); Tsai et al., *J. Clin. Periodontol.* 8:338 (1981). These sera were tested individually by a modified ELISA procedure (Ebersole, *J. Peridont. Res.* 15:621 (1980)) using French-press disrupted cell extracts of Aa strain HK1651 (ATCC Accession No. 700685) to verify that they retained their reactivity to Au. HK1651 is a member of the clonotype distinguished by a 530 bp deletion in the promoter region of the leukotoxin gene, and which has been characterized as being particularly virulent and contagious. Haubek et al. *J. Clin. Microbiol.* 34:1576 (1996). Equal amounts (0.05 ml) of each patient's serum were then pooled. Pooled sera from patients were utilized in this instance to maximize the spectrum of antibodies reactive with Aa epitopes, including immunodominant ones.

Antibodies in the pooled serum that were reactive with proteins made by Aa HK1651 during in vitro cultivation were eliminated by repeated adsorbtions using the methods of Brady et al., *J. Infect. Dis.* 158:965-972 (1988). Adsorbtions were performed using both whole cells and cell extracts immobilized on nitrocellulose. Briefly, 500 μl of the pooled sera were subjected to five successive adsorbtions against in vitro grown whole cells of Aa strain HK1651. The cells were grown in BHI broth at 37° C. in ambient atmosphere enriched with 5% $CO_2$. Each adsorbtion consisted of an overnight incubation of the pooled sera with approximately $10^{11}$ bacteria in 100 μl phosphate buffered saline (PBS, pH 7.2) containing 0.02% sodium azide with mild agitation at 4° C. The serum was further adsorbed by incubation overnight at 4° C. with a nitrocellulose membrane (10 cm diameter) saturated with HK1651 extracts prepared by French-press treatment of $10^{11}$ in vitro grown Aa cells. A final adsorbtion step was carried out using the same extract which was heat denatured in a boiling water bath (10 min.) before immobilization on nitrocellulose in order to expose additional immunoreactive epitopes.

Figure 2:
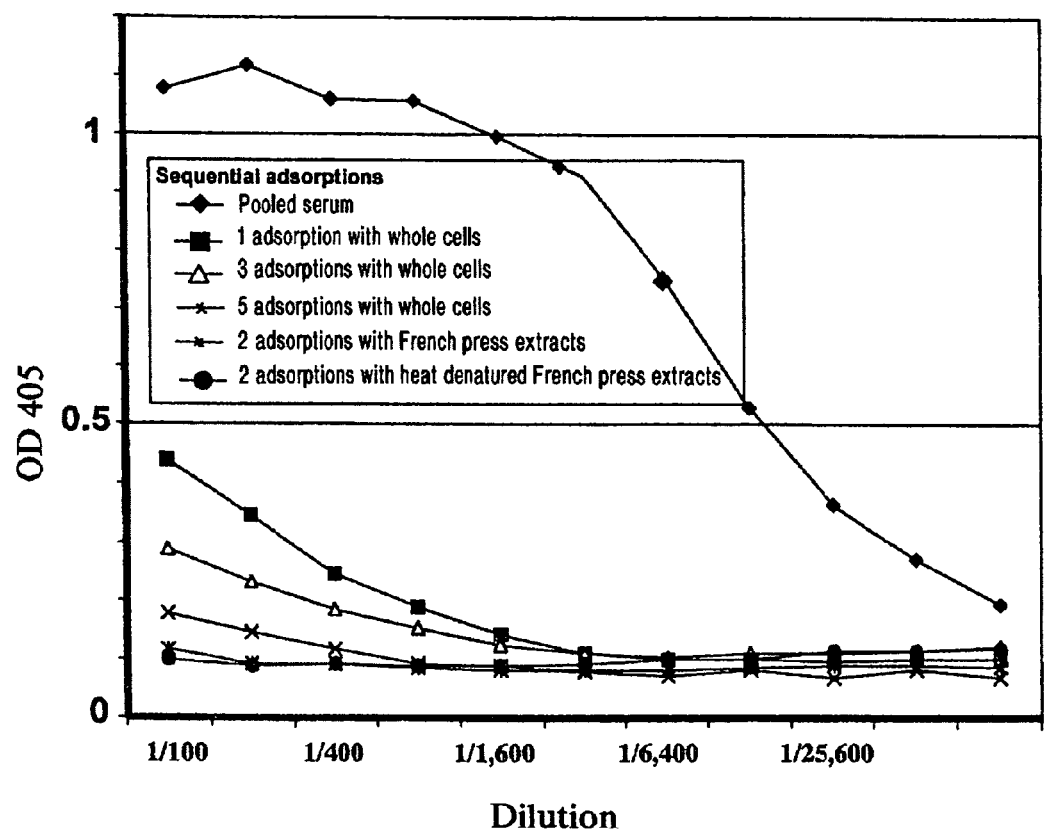
FIG. 2 shows sequential adsorbtion of pooled serum to eliminate antibodies reactive with in vitro expressed antigens. The pooled sera were subjected to five successive adsorbtions with whole cells, two adsorbtions with French press extracts, and two adsorbtions with heat denatured French press extracts.

To evaluate the efficiency of the adsorbtion steps, French-press cell extracts of HK1651 were immobilized in microtiter wells and, following a modified ELISA procedure (Ebersole, 1980), were reacted with serial dilutions of serum samples taken at different points in the adsorbtion process. Peroxidase-conjugated goat anti-human affinity-purified immunoglobulin (ICN Cappel; Aurora Ohio), reactive with all classes of human immunoglobulins, was used to determine the reactive antibody titers. As shown in FIG. 2, the successive adsorbtions essentially removed all of the antibodies reactive with in vitro grown HK1651. In preliminary studies it was determined that it was unnecessary to adsorb the serum with the *Escherichia coli* host strain since it produced a relatively low background signal.

EXAMPLE 2

Expression Library Construction and Screening with LJP Serum

Genomic expression libraries of HK1651 in PET30abc were prepared in *E. coli* strain BL21(DE3) (Novagen, Madison, Wis.). Briefly, genomic DNA purified from Aa strain HK1651 was partially digested with Sau3A to optimize the production of 0.5 to 1.5 kb fragments which were purified by agarose gel electrophoresis. The fragments were ligated into the multiple cloning site of pET30a inducible expression system (Novagen; Madison, Wis.) that had been digested with BamHI, dephosphorylated with calf intestinal phosphatase (New England Biolabs, Beverly, Mass.), and then transformed into *Escherichia coli* strain BL21(DE3) (Novagen). Similar libraries were also constructed with pET b and c.

The resulting HK1651 genomic expression library was serially diluted and plated on brain-heart infusion (BHI) medium containing kanamycin (50 μg/ml) to generate plates containing approximately 500 colonies per plate. These colonies were replicated using sterile velvet onto duplicate BHI plates containing kanamycin and IPTG (1 mM) and incubated for 5 hours at 37° C. to induce expression of the cloned polynucleotides. To lyse the bacteria the colonies were exposed to chloroform vapors for 15 min. and overlaid with nitrocellulose membranes for 15 min. at room temperature. The membranes were carefully removed and blocked with 5% non-fat skim-milk solution in PBS at pH 7.2 containing 0.5% Tween-20 (PBS-Tween™). The colonies were first probed with a 1:10,000 dilution of adsorbed serum (based on the results shown in FIG. 2) overnight at 4° C. and then with a 1:10,000 dilution of goat anti-human peroxidase conjugated antiserum under the same conditions. Reactive colonies were detected using the ECL kit and Hyperfilm™ ECL (Amersham Pharmacia Biotech, Piscataway N.J.). X ray film exposure times were adjusted to optimize signal to noise.

Figure 3A:
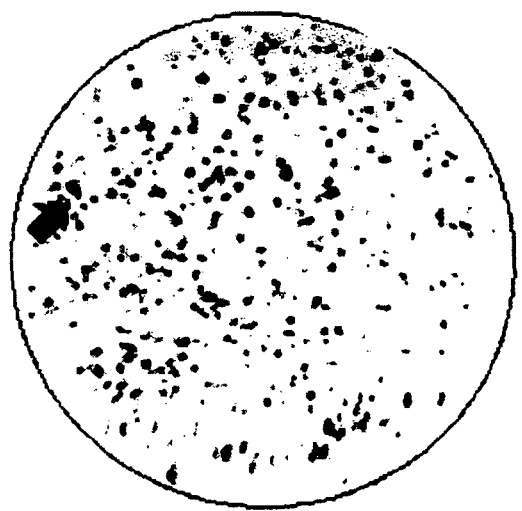
FIG. 3 shows the probing of a partial genomic library. Plates containing appropriate numbers of colonies were replicated onto medium with IPTG to induce expression of the cloned fragments. The colonies were lifted onto duplicate membranes, which were then reacted with either the pooled unadsorbed (panel A) or pooled adsorbed (panel B) sera. Reactive clones were visualized by probing with peroxidase-conjugated goat anti-human immunoglobulin as a secondary reagent followed by development with a chemiluminescent substrate and autoradiography.
Figure 3B:
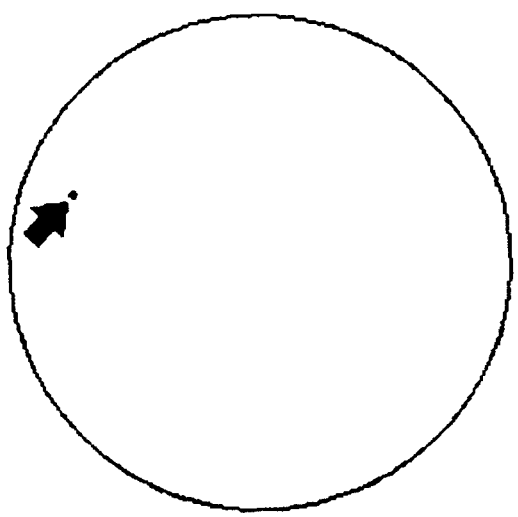

FIG. 3 demonstrates the reactivity observed when replica colony blots were probed in parallel with either unadsorbed or adsorbed pooled serum. Plates containing appropriate numbers of colonies were replicated onto medium with IPTG to induce expression of the cloned fragments. The colonies were lifted onto duplicate membranes, which were then reacted with either the pooled unadsorbed (panel A) or pooled adsorbed (panel B) sera. Reactive clones were visualized by probing with peroxidase-conjugated goat anti-human immunoglobulin as a secondary reagent followed by development with a chemiluminescent substrate and autoradiography.

The majority of clones reacted with the pooled unadsorbed serum, indicating that periodontitis patients had produced antibodies that recognized a broad array of *A. actinomycetemcomitans* proteins. Only a small subset of colonies tested (13 out of 20,000 screened) reacted with the pooled adsorbed serum. These IVIAT clones were isolated.

Potential bias created by using a single restriction enzyme is eliminated by using a second restriction enzyme (e.g., MboI), DNA sheared by a HydroShear™ apparatus (GeneMachines, San Carlos Calif.), or sonically sheared DNA to create a second, independent expression library in, for example, pET30abc. In the latter case, purified HK1651 DNA at a concentration of approximately 1 µg/µl is treated on ice with 3 second resonance frequency bursts of sonication using a Microson Ultrasonic Cell Distruptor (Heat Systems-Ultrasonics, Inc.). Samples taken at each time point are analyzed by agarose gel electrophoresis to determine the conditions required to optimize production of 0.75 to 1.5 Kb fragments. These conditions are employed in a large scale experiment to generate sufficient starting material for library construction. Terminal overhangs are removed with Klenow and dNTPs and the resulting blunt end products are ligated into the dephosphorylated EcoRV restriction site in the pET30abc multiple cloning site. The vector library is then be transformed into *E. coli* host strain, BL21 (DE3), with clones selected on BHI/kanamycin medium as previously described. Plates containing appropriate numbers of colonies are probed with the adsorbed serum and reactive colonies are detected using peroxidase-labeled goat anti-human immunoglobulin. Reactive colonies are isolated and their vector DNA purified.

EXAMPLE 3

Characterization of Polynucleotide Clones Reactive with Adsorbed LIP Serum

Sequencing of the cloned inserts in both directions indicated that the 13 recovered clones consisted of 8 unique clones. See SEQ ID NOs:1-8. MacVector v.6.0.1 was used to identify open reading frames using both Fickett's and start/stop codon methods. In every instance, potential open reading frames were present on the cloned inserts oriented in both the same and opposite direction relative to the pET promoter (Table 1).

In order to determine which of these was most likely to be the one encoding the antigen reactive with the adsorbed serum, a colony lift method was first used to determine if the level of expression of the antigen was regulated by IPTG. Briefly, Each IVIAT clone was grown overnight at 37° C. in BHI broth containing kanamycin, the cells were concentrated 200-fold, and 1 µl of each culture was spotted on BHI agar plates containing kanamycin with or without IPTG. Following incubation of the plates at 37° C. for five hours, the colonies were partially lysed with chloroform vapors, lifted onto nitrocellulose membranes, and reacted with the adsorbed serum. Two negative controls were included in this IPTG induction assay, namely pET30a/BL21(DE3) with no cloned insert and a randomly selected clone (IVIAT-47) which contained a cloned DNA insert, but was non-reactive with the adsorbed serum.

This assay demonstrated that 6 of the 8 IVIAT clones expressed immunoreactive proteins that were induced by IPTG. See Table 1 and SEQ ID NO:9, SEQ ID NO:11, SEQ ID NO:13, SEQ ID NO:15, SEQ ID NO:17, and SEQ ID NO:19). Therefore, their open reading frames of interest were likely cloned in the same orientation as the endogenous pET30 promoter. Their translation may either be initiated at the pET30 ribosome binding site or at their own ribosome binding site. We further examined 6 of the 11 possible open reading frames found in the IPTG inducible clones (Table 2). Each of these open reading frames was individually amplified by PCR and subcloned so that it was in-frame and under control of the pET30EkLIC (Novagen, Madison, Wis.) IPTG regulated promoter. See SEQ ID NO:10, SEQ ID NO:12, SEQ ID NO:14, SEQ ID NO:16, SEQ ID NO:18, and SEQ ID NO:20. Reactivity with the adsorbed serum and IPTG inducibility of these subclones was confirmed using the colony lift method used previously (Table 2). Four polynucleotides with demonstrable homology were found, including one (Aa2004) that is related to a known virulence factor (hlpA) in the closely related organism, *Haemophilus influenza*. There are three examples of polynucleotides with homology to genes encoding proteins with known function but with previously undemonstrated relevance to pathogenesis (Aa2005; Aa2009; Aa20011). Two polynucleotides were found with no homologues identified to date (Aa2008; Aa20010). These types of in vivo induced polynucleotides may well represent entirely novel virulence factors of Aa. Interestingly, none of the open reading frames thus far identified on the clones isolated by this invention show homology to genes with known housekeeping functions. The reason for this difference is uncertain, but this represents an important additional advantage of the method described herein.

EXAMPLE 4

Verification of Specific In Vivo Expression

It is possible to directly verify that in vivo induced antigens identified by IVIAT are actually expressed by the pathogen when it is growing at the site of infection in the human host. To accomplish this, a method to directly probe biological specimens taken from disease sites of infected patients was developed. The first step in this process involved optimization of recombinant protein production by the subclones obtained in the previous step. Clone Aa2008 contains a 495 bp open reading frame (SEQ ID NO:13) for a hypothetical protein subcloned into pET30EkLIC (Table 2). Including the 5' and 3' sequences added by the vector, the molecular weight of the translated product should be approximately 28 Kda. Aa2008 was incubated in BHI broth containing kanamycin and IPTG (5 mM). Samples of the culture were removed at hourly intervals and analyzed by SDS-PAGE to determine the incubation time required for maximum production of the cloned protein. A major band (not seen in pET30EkLIC/BL21(DE3) control samples) was found that had the expected molecular weight. Based on the results obtained, inclusion body preparations (Harlow & Lowes Eds., *Antibodies, a Laboratory Manual*, (CSHL Press, Plainview, N.Y., 1988)) were made from 10 ml batch cultures of Aa2008 incubated for 3 hours with IPTG. SDS-PAGE and Western blot analysis was performed to confirm that the overexpressed protein was reactive with the adsorbed serum used in the original screening. The reactive band was excised from the Coomassie stained gel and used to raise polyclonal antibodies in mice.

Three female Balb/C mice are used per antigen. The 6-8 week old mice were injected subcutaneously (sc) with the purified polypeptide, using a concentration of 20, 50, or 100 µg/mouse. RIBI MPL+TDM emulsion was used an adjuvant. Two weeks later, the immunization protocol was repeated. Approximately 10 days after the second immunization, a small amount of blood was taken from the tail vein of each mouse, and assayed by ELISA to evaluate the response to the immunogen. Where the mice were responding well (i.e., detection at serum dilution greater than 1:500), one more sc injection was given 3-4 weeks after the second immunization, and four days before the scheduled hybridoma fusion. A mouse myloma cell line (Sp2/0) was cultured for several days prior to the scheduled fusion. Log phase cells were counted and washed.

The mouse exhibiting the best serum titer was anesthetized and bled out. The spleen was removed. The blood was clotted and spun down and the serum saved to be used as a positive control in the subsequent assays. The spleen cells were flushed out of the spleen capsule and separated into single cells, washed, and counted. Spleen cells were combined with Sp2/0 cells at a 7:1 ratio. Cells were pelleted by centrifugation. PEG 1500 at a concentration of 50% was slowly added to the cell pellet and then diluted. Cells were spun down and the pellet resuspended in HAT selective medium containing 20% horse serum and 25% conditioned media. Cells were plated into 96 well plates at a concentration of $2.5 \times 10^5$ cells/well. Cells were grown in a 37° C. incubator with 7% atmospheric $CO_2$ After several days, colonies of hybridoma cells were visible. Feeding (removing and replacing approximately 50% of the total volume of growth medium) was performed at day seven and again at day nine or ten. When the hybridoma cells were nearly confluent in each well, a portion of the supernatant was removed and assayed by ELISA to detect the presence of the desired antibody. The cells in the wells that tested positive on the primary screen were transferred to a 24 well plate, and the supernatant tested again by ELISA. The antibody activity and preliminary heavy chain isotype of each mass culture was determined and the wells that scored positive during this secondary round of screening were transferred to 6 well plates. At this point the cells were designated as mass cultures. Each mass culture chosen was cultured briefly in 6 well plate wells in order to freeze two vials of cells. Supernatant was saved for future expanded screening. The best mass cultures were selected for ascites production. Ascites were induced by intraperitoneal injection into one female Balb/C mouse, which was monitored daily for 7 days. The ascitic fluids were collected every day for 3 days (for a final volume of ca. 10 ml).

Ascites fluid were filtered and circulated over a protein A affinity column to affinity purify IgG. The polyclonal antibodies were washed and eluted with 0.1 M glycine, pH 3.0, followed by neutralization with Tris, pH 9-10. The recovered antibodies were concentrated, and the buffer exchanged to 1×PBS with 0.02% azide. The yield and quality of the antibodies were evaluated spectrophotometrically (280 nm) and by SDS-PAGE, respectively.

The purified IgG was shown to react in western blots with a protein of the appropriate size in extracts and inclusion body preparations made from clone Aa2008. The antibodies were labeled directly with fluorescein isothiocyanate (FITC) (Molecular Probes, Eugene, Oreg., USA). A murine monoclonal antibody specific for Aa, Mab 13(10B2), was labeled with Texas-red (TR).

Subgingival plaque from patients with LJP was sampled at the time of their diagnosis. Sterile paper points were inserted into mesial, buccal and distal sites of all four first molars that had significant (greater than or equal to 5 mm) bone loss. The points were immediately immersed in ice-cold BHI broth containing 50% glycerol, and after removing a small sample for microbiological identification of Aa, they were quick frozen in a dry ice/ethanol bath and stored at −80° C. Samples which were confirmed to contain Aa by growth on selective medium were used to directly demonstrate the presence of Aa2008.

Plaque samples and matched in vitro grown cells were assayed by immunofluorescence microscopy (FIG. 4). Briefly, plaque samples were thawed on ice, homogenized by brief vortexing at 4° C., and immediately heat-fixed on microscope slides. Plaque samples and matched in vitro grown Aa isolates taken from the selective medium were probed in parallel with ETC-labeled monospecific antibody directed against antigen Aa2008 and the TR-labeled Aa-specific monoclonal antibody. Samples were examined by fluorescence microscopy (excitation wavelength 488 nm). Double color analysis, using matched differential emission filters, was performed to identify individual cells that were simultaneously labeled with FITC and TR. Bacterial cells in plaque that reacted with TR-labeled anti-Aa monoclonal antibody (FIG. 4A) also reacted with FITC-labeled anti-Aa2008 antibody (FIG. 4B) and these signals were found to colocalize (FIG. 4C). In contrast, matched in vitro grown Aa reacted with the TR-labeled anti-Aa monoclonal antibody (FIG. 4D), but not with FITC-labeled anti-Aa2008 antibody (FIG. 4E) and therefore no colocalization was observed (FIG. 4F). These results provide direct evidence that Aa expresses antigen Aa2008 exclusively during in vivo growth.

Each anti-IVIAT antibody may independently screened against all of the plaque samples collected (3 samples/tooth× maximum 4 teeth/patient×10 patients≦120 samples) in order to optimize the identification of Aa growing under environmental conditions appropriate for expression of the in vivo induced antigen. Aa-deficient samples are included to serve as an additional negative control for the species specific antibody and to identify possible cross-reacting antigens presented by other species that may be present in plaque. Based on our previous studies, we expect that approximately 75% of samples will contain measurable numbers of Aa. Of the three most likely outcomes, there will be instances where cells react with Texas red-labeled anti-Aa antibody and one or all of these cells also react with a FITC-labeled anti-IVIAT antibody. This indicates that particular antigen is produced by Aa during growth in a site of infection. There is no requirement for all of the Aa cells in a sample to react with the anti-IVIAT antibody since there are likely to be numerous microenvironments present at each sampling site. As a second possible outcome, there may be instances where none of the cells which react with the Texas red-labeled anti-Aa antibody also react with a particular FITC-labeled anti-IVIAT antibody. This indicates that none of the plaque samples were taken from sites presenting the necessary environmental stimulus. Clearly, by using a large number of plaque samples taken from patients in different stages of infection, we hope to reduce the occurrence of this possibility. This result may also indicate that the in vivo induced antigen was expressed but not surface localized. Thus, in situations where a particular anti-IVIAT antibody does not react with Aa cells in any of the plaque samples, one may examine intra- and extra-cellular compartments for the antigen. This is done simply by examining plaque sample homogenates using a capture ELISA method: microtiter wells are coated with unlabeled anti-IVIAT antibody, reacted with homogenate, and then probed with FITC-labeled anti-IVIAT antibody according to Current Protocols in Immunology, John Wiley & Sons, NY (1998). The presence of reactivity, as measured by fluorescent light emission, is then correlated to the presence of Aa as determined by prior microbiological, ribotyping and immunological analyses of the plaque samples. As another possible outcome of interest, plaque samples may contain cells that react with a particular FITC-labeled anti-IVIAT antibody but which do not react with Texas red-labeled anti-Aa antibody. These are likely to represent instances where plaque samples contain other bacterial species which produce a cross-reacting antigen. However, it is also possible that these cells belong to a strain or variant of Aa which does not react with the species anti-Aa antibody. In these instances, previous culturing data along with ribotyping verification will help us to distinguish between these possibilities.

As an alternative approach to the microscopy methods described above, one may use FITC-labeled anti-IVIAT antibodies and a fluorescence-activated cell sorting system (e.g., FACSort, Becton Dickinson; Franklin Lanes, N.J.). Recent reports have demonstrated the technical feasibility of using automated cell sorters for separating bacteria (Valdivia & Falkow, *Science*, 277:2007 (1997); Handfield & Levesque, *FEMS Microbiol. Rev.* 23:69-91 (1999). In addition, FACS can be used to effectively separate Aa from a mixed bacterial population using the green fluorescence protein (GFP) as a gene marker. In this study, a strain of Aa (SUNY 465) expressing the GFP under the leukotoxin ltx promoter was separated from Aa strain Y4 with the FACSort.

EXAMPLE 5

Screening Patients for Reactive Antibodies

Figure 5:
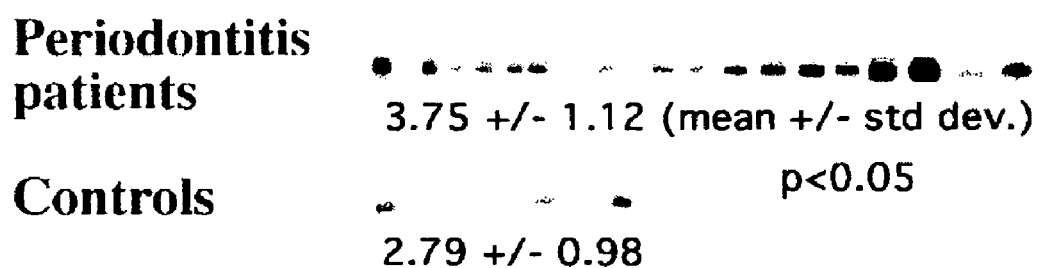
FIG. 5 shows western blot analysis of immunoreactivity of patient and control subjects' sera to Aa2008. Western blots of the inclusion body preparation of Aa2008 were probed using individual, unadsorbed sera from 20 periodontitis patients and 9 control subjects.

Once IVIAT has identified and confirmed an in vivo induced antigen, the purified antigen can be used to screen the sera of individual patients for reactive antibodies. Western blots of the inclusion body preparation of Aa2008 were probed using individual, unadsorbed sera from 20 periodontitis patients and 9 control subjects (FIG. 5). Densitometric analysis of Western blots showed that the patient group demonstrated significantly ($p<0.05$, independent student's T-test) higher reactivity with the recombinant Aa2008 protein ($3.75\pm1.12$, mean±standard deviation) than a control group that did not have periodontitis ($2.79\pm0.98$). These data suggest that Aa2008 is immunogenic in periodontitis patients, and confirms the conclusion drawn from fluorescence microscopy of plaque samples that this represents an in vivo expressed polynucleotide.

---

We claim:

1. A method of isolating clones comprising a polynucleotide of a microbe or pathogen that is expressed only in vivo comprising:
    (a) obtaining an antibody sample from one or more hosts naturally infected with the microbe or pathogen;
    (b) adsorbing the antibody sample with in vitro grown cells or cellular extracts of the microbe or pathogen;
    (c) isolating unadsorbed antibodies; and
    (d) probing an expression library of clones of the microbe or pathogen with the unadsorbed antibodies of (c) and isolating clones from the expression library to which the unadsorbed antibodies bind;
        wherein clones comprising a polynucleotide of the microbe or pathogen that is expressed only in vivo are isolated.

2. The method of claim 1 wherein the polynucleotides of the microbe or pathogen that are expressed only in vivo encode in vivo induced antigens.

3. The method of claim 2 wherein the in vivo induced antigens are capable of eliciting an immune response in an animal.

4. The method of claim 3 wherein the animal is selected from the group consisting of humans, baboons, chimpanzees, macaques, cattle, sheep, pigs, horses, goats, dogs, cats, rabbits, guinea pigs, rats, mice, chickens, ducks, and fish.

5. The method of claim 1 further comprising the step of determining the nucleic acid sequence of the polynucleotide.

6. The method of claim 1 wherein the antibody sample of (a) is sera from the one or more hosts infected with the microbe or pathogen.

7. The method of claim 6, wherein the one or more hosts are an animal selected from the group consisting of humans, baboons, chimpanzees, macaques, cattle, sheep, pigs, horses, goats, dogs, cats, rabbits, guinea pigs, rats, mice, chickens, ducks, and fish.

8. The method of claim 1 wherein the microbe or pathogen is selected from the group consisting of a bacterium, a virus, a parasite, a prion, and a fungus.

9. The method of claim 1 wherein the microbe or pathogen is selected from the group consisting of *Candida, Aspergillus, Sporothrix, Blastomyces, Histoplasma, Cryptococcus, Pneumocystis, Coccidioides, Tinea, Toxoplasma, Plasmodium, Pseudomonas, Actinobacillus, Staphylococcus, Bacillus, Clostridium, Listeria, Corynebacterium, Actinomyces, Mycoplasma, Nocardia, Bordetella, Brucella, Francisella, Legionella, Enterobacter, Escherichia, Klebsiella, Proteus, Salmonella, Shigella, Streptococcus, Yersinia, Vibrio, Campylobacter, Helicobacter, Bacteroides, Chlamydia, Borrelia, Treponema, Leptospira, Aeromonas, Rickettsia, Ascaris, Cryptosporidium, Cyclospora, Entamoeba, Giardia, Shistosoma, Trypanosoma,* herpes virus, cytomegalovirus, Epstein-Barr virus, hepatitis virus, adenovirus, papillomavirus, polyomavirus, enterovirus, rotavirus, influenza virus, paramyxovirus, rubeola virus, rhabdovirus, human immunodeficiency virus, arenavirus, rhinovirus, and reovirus.

10. The method of claim 1, wherein the microbe is a bacterium or a fungus.

11. The method of claim 1, wherein the one or more hosts infected with the microbe or pathogen is a human.

12. The method of claim 1, wherein an antibody sample is obtained from more than one host naturally infected with the microbe or pathogen and wherein the hosts are infected by the pathogen by more than one route of infection.

13. The method of claim 1, wherein an antibody sample is obtained from more than one host naturally infected with the microbe or pathogen and wherein the hosts are in different phases of infection by the pathogen.

14. The method of claim 1, wherein an antibody sample is obtained from more than one host naturally infected with the microbe or pathogen and wherein the hosts are infected by different clonal variants or different strains of the pathogen.

15. The method of claim 1 further comprising:
    (e) expressing and isolating a polypeptide from the isolated polynucleotide of claim 1;
    (f) producing antibodies to the polypeptide; and
    (g) demonstrating that the antibodies are reactive with biological samples from disease sites from a host naturally infected with the microbe or pathogen, but not reactive with cells or cellular extracts of the microbe or pathogen that have been grown in vitro; whereby the isolated polynucleotide is confirmed as being expressed only in vivo.

16. A method of comparing polynucleotides of a microbe or pathogen that are expressed only in vivo and at different stages of infection of the microbe or pathogen comprising the steps of:
    (a) obtaining a first antibody sample from one or more hosts naturally infected with the microbe or pathogen, wherein each host is in about the same stage of the infection;
    (b) adsorbing the first antibody sample with cells or cellular extracts of the microbe or pathogen that have been grown in vitro;
    (c) obtaining a second antibody sample from one or more hosts naturally infected with the microbe or pathogen, wherein each host is in about the same stage of the infection, wherein the stage of the infection is different from the stage of infection in step (a);
    (d) adsorbing a the second antibody sample with cells or cellular extracts of the microbe or pathogen that have been grown in vitro;
    (e) isolating unadsorbed antibodies from the first antibody sample and from the second antibody sample;
    (f) probing a first expression library of clones of the microbe or pathogen with the unadsorbed antibodies from the first antibody sample and isolating clones from the first expression library to which the unadsorbed antibodies bind, and probing a second expression library of clones of the microbe or pathogen with the unadsorbed antibodies from the second antibody sample and isolating clones from the second expression library to which the unadsorbed antibodies bind, wherein polynucleotides of the microbe or pathogen that are expressed only in vivo are isolated for the first and second antibody sample; and (g) comparing the polynucleotides of the microbe or pathogen that are expressed only in vivo and at different stages of infection of the microbe or pathogen.

17. The method of claim 16 wherein the first expression library and the second expression library are the same expression library.

18. A method of comparing polynucleotides of a microbe or pathogen that are expressed only in vivo, wherein the microbe or pathogen has naturally infected its host by different routes of infection comprising the steps of:

(a) obtaining a first antibody sample from one or more hosts naturally infected with the microbe or pathogen, wherein each host has been naturally infected by about the same route of infection;

(b) adsorbing the first antibody sample with cells or cellular extracts of the microbe or pathogen that have been grown in vitro;

(c) obtaining a second antibody sample from one or more hosts infected with the microbe or pathogen, wherein each host has been infected by about the same route of infection, wherein the route of infection is different from the route of infection in step (a);

(d) adsorbing the second antibody sample with cells or cellular extracts of the microbe or pathogen that have been grown in vitro;

(e) isolating unadsorbed antibodies from the first antibody sample and from the second antibody sample;

(f) probing a first expression library of clones of the microbe or pathogen with the unadsorbed antibodies from the first antibody sample and isolating clones from the first expression library to which the unadsorbed antibodies bind, and probing a second expression library of clones of the microbe or pathogen with the unadsorbed antibodies from the second antibody sample and isolating clones from the second expression library to which the unadsorbed antibodies bind, wherein polynucleotides of the microbe or pathogen that are expressed in vivo are isolated for the first and second antibody sample; and (g) comparing the polynucleotides of the microbe or pathogen that are expressed only in vivo by different routes of infection of the microbe or pathogen.

19. The method of claim 18 wherein the first expression library and the second expression library are the same expression library.

20. A method of confirming an animal model of infection as a valid model comprising the steps of:

(a) obtaining a first antibody sample from one or more first animal model hosts naturally infected with a microbe or pathogen;

(b) adsorbing the first antibody sample with cells or cellular extracts of the microbe or pathogen that have been grown in vitro;

(c) obtaining a second antibody sample from one or more second hosts naturally infected with the microbe or pathogen, wherein the second host is a different species of animal than the first animal model host;

(d) adsorbing a the second antibody sample with cells or cellular extracts of the microbe or pathogen that have been grown in vitro;

(e) isolating unadsorbed antibodies from the first antibody sample and from the second antibody sample;

(f) probing a first expression library of clones of the microbe or pathogen with the unadsorbed antibodies from the first antibody sample and isolating clones from the first expression library to which the unadsorbed antibodies bind, and probing a second expression library of clones of the microbe or pathogen with the unadsorbed antibodies from the second antibody sample and isolating clones from the second expression library to which the unadsorbed antibodies bind, wherein polynucleotides of the microbe or pathogen that are expressed only in vivo are isolated for the first and second antibody sample; and (g) comparing the polynucleotides of the microbe or pathogen that are expressed only in vivo in the first animal model host and the second host; wherein if the polynucleotides expressed only in vivo in the first animal model and in the second host are the same or similar, then the first animal model is confirmed as a valid model.

21. The method of claim 20 wherein the first expression library and the second expression library are the same expression library.

22. The method of claim 20 wherein the first animal model host and the second host are selected from the group consisting of humans, baboons, chimpanzees, macaques, cattle, sheep, pigs, horses, goats, dogs, cats, rabbits, guinea pigs, rats, mice, chickens, ducks, and fish.

* * * * *

SEQUENCE LISTING

```
<160> NUMBER OF SEQ ID NOS: 20

<210> SEQ ID NO 1
<211> LENGTH: 849
<212> TYPE: DNA
<213> ORGANISM: Actinobacillus actinomycetemcomitans
<220> FEATURE:
<221> NAME/KEY: misc_feature
<222> LOCATION: (566)..(566)
<223> OTHER INFORMATION: N stands for any nucleotide.
<220> FEATURE:
<221> NAME/KEY: misc_feature
<222> LOCATION: (625)..(625)
<223> OTHER INFORMATION: N stands for any nucleotide.
<220> FEATURE:
<221> NAME/KEY: misc_feature
<222> LOCATION: (627)..(627)
<223> OTHER INFORMATION: N stands for any nucleotide.
<220> FEATURE:
<221> NAME/KEY: misc_feature
<222> LOCATION: (636)..(636)
<223> OTHER INFORMATION: N stands for any nucleotide.
<220> FEATURE:
<221> NAME/KEY: misc_feature
<222> LOCATION: (650)..(650)
<223> OTHER INFORMATION: N stands for any nucleotide.
<220> FEATURE:
<221> NAME/KEY: misc_feature
<222> LOCATION: (656)..(656)
<223> OTHER INFORMATION: N stands for any nucleotide.
<220> FEATURE:
<221> NAME/KEY: misc_feature
<222> LOCATION: (661)..(661)
<223> OTHER INFORMATION: N stands for any nucleotide.
<220> FEATURE:
<221> NAME/KEY: misc_feature
<222> LOCATION: (672)..(672)
<223> OTHER INFORMATION: N stands for any nucleotide.
<220> FEATURE:
<221> NAME/KEY: misc_feature
<222> LOCATION: (681)..(681)
<223> OTHER INFORMATION: N stands for any nucleotide.
<220> FEATURE:
<221> NAME/KEY: misc_feature
<222> LOCATION: (720)..(720)
<223> OTHER INFORMATION: N stands for any nucleotide.
<220> FEATURE:
<221> NAME/KEY: misc_feature
```

-continued

<222> LOCATION: (723)..(723)
<223> OTHER INFORMATION: N stands for any nucleotide.

<400> SEQUENCE: 1

| | | | | | | |
|---|---|---|---|---|---|---|
| gatcgcgtaa | acggtgtaac | acggaaagca | attgtttaat | gtcggcaaaa | tgcagccctg | 60 |
| tggtcggttc | gtccagaata | tacagggttt | tgcccgtatc | ccgtttggag | agttccgtcg | 120 |
| ccagtttcac | ccgttgcgct | tccccgccgg | acagggtggt | agaggattgc | cccaagcgaa | 180 |
| tataagacaa | gcccacgtca | atcagggttt | gcaatttacg | cgcaatcatt | ggaatggcat | 240 |
| cgaaaaactc | gcgcgcatct | tccaccgtca | tgtccagcac | ctgatgaatg | gttttacctt | 300 |
| tgtagcggat | ttccagggtt | tcgcgattgt | aacgcttgcc | tttacattgg | tcgcaaggca | 360 |
| cgtacacatc | gggcaggaag | tgcatttcca | ctttgattac | gccgtcgccc | tggcaggctt | 420 |
| acagcgcccg | ccgcgcacgt | taaaactgaa | acgccccggg | ttataaccgc | gcgcacgggc | 480 |
| tttcggtacg | ccggcaaaca | attcgcgaat | cggcgtgaat | acgcccgtgt | aagttgcccg | 540 |
| gttggagcgt | ggcgtgcgtc | caatcnggct | ttggttaata | tcaatacttt | atcgaaaaat | 600 |
| tccaaacctt | taatggactt | gtacngngaa | acctcngcat | tttctgcacn | attaangcgt | 660 |
| nttgtgcaat | anggaacaaa | ntgtcgttaa | tcagtgtaga | atttaccttha | accggacacn | 720 |
| ccngtgatgc | aggtaaataa | gcccacggga | atgtctaaat | tgacgttttt | caggttgtta | 780 |
| ccggaagcgc | cgaacaattt | gagcattttt | ttcttatcaa | gtgcggtacg | ttttttcggt | 840 |
| atttcgatc | | | | | | 849 |

<210> SEQ ID NO 2
<211> LENGTH: 357
<212> TYPE: DNA
<213> ORGANISM: Actinobacillus actinomycetemcomitans

<400> SEQUENCE: 2

| | | | | | | |
|---|---|---|---|---|---|---|
| gatcactaag | ttgttcaatc | ctttcgcttg | ggaatctttg | tctaaatacg | gtttatgttg | 60 |
| cattgcgtta | acgtctaaat | cacctttaga | cactgcagtg | tttggcaagg | cgtagtcatg | 120 |
| aataaaacgt | attctacgtc | taagttgtat | ttttcttttg | ccactttcgc | tgcgatttca | 180 |
| gccacttggt | gttccggtcc | tgccatcacg | cccactttga | ttgttgccgg | ggcttctgcc | 240 |
| gccggtttgt | ctgccggtgc | ggcttccggt | tttttctctt | cattacaagc | ccgttaaggc | 300 |
| gaatacggag | gctaatgttg | cgacgcctaa | taattttttt | caagttcata | aaagatc | 357 |

<210> SEQ ID NO 3
<211> LENGTH: 886
<212> TYPE: DNA
<213> ORGANISM: Actinobacillus actinomycetemcomitans
<220> FEATURE:
<221> NAME/KEY: misc_feature
<222> LOCATION: (554)..(554)
<223> OTHER INFORMATION: N stands for any nucleotide
<220> FEATURE:
<221> NAME/KEY: misc_feature
<222> LOCATION: (596)..(596)
<223> OTHER INFORMATION: N stands for any nucleotide

<400> SEQUENCE: 3

| | | | | | | |
|---|---|---|---|---|---|---|
| gatcaaactg | gtggcgcaag | ggcagcgcgt | agcaaattta | cccgatattt | tggtctatgc | 60 |
| gcgcgtcggc | aacggcatgg | tagggcgacg | ccgtggttta | aaccaagcca | aagcggaatg | 120 |
| gcgcttattt | aagctaaaac | accatcttgg | cattcaggga | ttttatccg | ggctattcac | 180 |
| ttttgtcctg | cgttccggtg | ccagattatt | gccgacatca | ttactgaaaa | acatctatca | 240 |
| aaccttttta | agaaaataac | atgatgaaat | taaactgtat | tttaaaaata | tccggaattt | 300 |

```
ccaccgcact ttttctagcg ggttgttcct caaattcaag tgcgccgacg caatcctctg    360
agcaggcgaa ttctgttacg gctgtgaatc ccactgcggt gtacagtaag ccccgcactt    420
tggataactt caacgattat gtgaatttct taaaaggtaa agcagcggca gaaggcgttt    480
ctgccgacgt attgaatgca caaaataata ttaattatat tcaaaaatcc gtggatttgg    540
acgatcaaca agcnggcaga attcgcaagc gtgatccaaa tgccccgccg atcatnaatt    600
ccgaacggca cgaccaatta cttaaatcgt gtattaacca agaataaagt agacacggca    660
gaagcacgtt attgggaaca attgccgcag cttgaaaatg cttcaaagaa attcagcgta    720
ccgaaaaatt atctgttagc cttgtggggc atggagagta gctttggcta ttatcagggc    780
aattacgatg tgttatccac cttagccact cttgcttttg acggacgccg tgaagcctta    840
ttcagcaaag aattcatcgc cgccatgaaa atgctacagc gcgatc                   886
```

```
<210> SEQ ID NO 4
<211> LENGTH: 507
<212> TYPE: DNA
<213> ORGANISM: Actinobacillus actinomycetemcomitans
<220> FEATURE:
<221> NAME/KEY: misc_feature
<222> LOCATION: (4)..(4)
<223> OTHER INFORMATION: N stands for any nucleotide.
<220> FEATURE:
<221> NAME/KEY: misc_feature
<222> LOCATION: (9)..(9)
<223> OTHER INFORMATION: N stands for any nucleotide.
<220> FEATURE:
<221> NAME/KEY: misc_feature
<222> LOCATION: (21)..(21)
<223> OTHER INFORMATION: N stands for any nucleotide.
<220> FEATURE:
<221> NAME/KEY: misc_feature
<222> LOCATION: (23)..(23)
<223> OTHER INFORMATION: N stands for any nucleotide.
<220> FEATURE:
<221> NAME/KEY: misc_feature
<222> LOCATION: (29)..(29)
<223> OTHER INFORMATION: N stands for any nucleotide.
<220> FEATURE:
<221> NAME/KEY: misc_feature
<222> LOCATION: (32)..(32)
<223> OTHER INFORMATION: N stands for any nucleotide.
<220> FEATURE:
<221> NAME/KEY: misc_feature
<222> LOCATION: (35)..(36)
<223> OTHER INFORMATION: N stands for any nucleotide.
<220> FEATURE:
<221> NAME/KEY: misc_feature
<222> LOCATION: (39)..(39)
<223> OTHER INFORMATION: N stands for any nucleotide.
<220> FEATURE:
<221> NAME/KEY: misc_feature
<222> LOCATION: (42)..(42)
<223> OTHER INFORMATION: N stands for any nucleotide.
<220> FEATURE:
<221> NAME/KEY: misc_feature
<222> LOCATION: (45)..(45)
<223> OTHER INFORMATION: N stands for any nucleotide.
<220> FEATURE:
<221> NAME/KEY: misc_feature
<222> LOCATION: (49)..(49)
<223> OTHER INFORMATION: N stands for any nucleotide.
<220> FEATURE:
<221> NAME/KEY: misc_feature
<222> LOCATION: (52)..(52)
<223> OTHER INFORMATION: N stands for any nucleotide.
<220> FEATURE:
<221> NAME/KEY: misc_feature
<222> LOCATION: (58)..(58)
<223> OTHER INFORMATION: N stands for any nucleotide.
<220> FEATURE:
<221> NAME/KEY: misc_feature
```

<222> LOCATION: (61)..(62)
<223> OTHER INFORMATION: N stands for any nucleotide.
<220> FEATURE:
<221> NAME/KEY: misc_feature
<222> LOCATION: (65)..(65)
<223> OTHER INFORMATION: N stands for any nucleotide.
<220> FEATURE:
<221> NAME/KEY: misc_feature
<222> LOCATION: (69)..(69)
<223> OTHER INFORMATION: N stands for any nucleotide.
<220> FEATURE:
<221> NAME/KEY: misc_feature
<222> LOCATION: (73)..(73)
<223> OTHER INFORMATION: N stands for any nucleotide.
<220> FEATURE:
<221> NAME/KEY: misc_feature
<222> LOCATION: (97)..(97)
<223> OTHER INFORMATION: N stands for any nucleotide.
<220> FEATURE:
<221> NAME/KEY: misc_feature
<222> LOCATION: (102)..(102)
<223> OTHER INFORMATION: N stands for any nucleotide.
<220> FEATURE:
<221> NAME/KEY: misc_feature
<222> LOCATION: (138)..(138)
<223> OTHER INFORMATION: N stands for any nucleotide.
<220> FEATURE:
<221> NAME/KEY: misc_feature
<222> LOCATION: (457)..(457)
<223> OTHER INFORMATION: N stands for any nucleotide.
<220> FEATURE:
<221> NAME/KEY: misc_feature
<222> LOCATION: (459)..(459)
<223> OTHER INFORMATION: N stands for any nucleotide.
<220> FEATURE:
<221> NAME/KEY: misc_feature
<222> LOCATION: (467)..(467)
<223> OTHER INFORMATION: N stands for any nucleotide.

<400> SEQUENCE: 4

```
ttgntaccnt agccgctgac nanaactanc angcnntgna tnatntcgna tnattaaanat    60
nngcnaggng cancagctta cctttgccga cggttcnctg tntgaaagcg ccattcgcaa   120
agtgccggtg gaggcggnga aaattcactc acttggtgcg gaaggcaatg atgtgggatt   180
gaaagcccat catggcgggt ggataaagcg ttatttttta tgtcggcaga tgcctttcct   240
gcgttaaatg cgttattaga cgaaaatttt tcgtatcagg acacagcagt ttacggcgag   300
aattttgtgg tttccgcgct gaatgaagat tccgtgtgtg tgggcgatat ttatcaaatc   360
ggctcctgcg tggtggaggt gtcgcagccg cgtaaacctt gtgagcgctt atcgaaaaat   420
accaataatc cgaacacgca acaaaccgtg tacgctcncg ctggtcnggc tggtatgtgc   480
cggtggtacc ccaaggggga aattcaa                                       507
```

<210> SEQ ID NO 5
<211> LENGTH: 1087
<212> TYPE: DNA
<213> ORGANISM: Actinobacillus actinomycetemcomitans
<220> FEATURE:
<221> NAME/KEY: misc_feature
<222> LOCATION: (622)..(622)
<223> OTHER INFORMATION: N stands for any nucleotide.
<220> FEATURE:
<221> NAME/KEY: misc_feature
<222> LOCATION: (642)..(642)
<223> OTHER INFORMATION: N stands for any nucleotide.
<220> FEATURE:
<221> NAME/KEY: misc_feature
<222> LOCATION: (661)..(661)
<223> OTHER INFORMATION: N stands for any nucleotide.
<220> FEATURE:
<221> NAME/KEY: misc_feature
<222> LOCATION: (669)..(669)
<223> OTHER INFORMATION: N stands for any nucleotide.

```
<220> FEATURE:
<221> NAME/KEY: misc_feature
<222> LOCATION: (685)..(685)
<223> OTHER INFORMATION: N stands for any nucleotide.
<220> FEATURE:
<221> NAME/KEY: misc_feature
<222> LOCATION: (690)..(690)
<223> OTHER INFORMATION: N stands for any nucleotide.
<220> FEATURE:
<221> NAME/KEY: misc_feature
<222> LOCATION: (700)..(700)
<223> OTHER INFORMATION: N stands for any nucleotide.

<400> SEQUENCE: 5
gatcgcaaca agcgcagttt ctatatttcc gccgcccgca gtgagatttt caatttaatc      60
gttgccaaac gtattgaact cagtctggcg cagcaggtct taaatggaga cgttttgcaa     120
ctgaacggtt cgcacagttg gtttgtggcg gacgcatcgg aagatttgac gcaactgcaa     180
caacgcttgg cacaacggga tattttgctt accgcaccgc ttatcggcga agaggacaaa     240
agtgcggtgg attttgagaa tgaaattttt gtcgcgcacc aagccttgtt ccatttgatg     300
cggcaagaac gcgtgaaagc cgcccgccgt ccgattttaa tgcaggcgca acagtttcaa     360
tggcaatttg aaccgaacgg tttgcgcctt aaatttatt tgccggcagg cagttacgcc      420
acggcgttgg tacgcgagct ggtgaatgtt gaaaactgaa aaacgagaag aaaaacagga     480
ataacaagaa catgaatatt ttattaagta acgatgacgg cattcacgcg ccgggcattc     540
gtgtgatggc agaacattgc gtaagattgc caatgtgacc atcgtcgcgc cggacagcaa     600
ccgcaagcgc cgccttcagt tncttaacct tggtgaagcc gntgtattcc gttcatttgg     660 naaagcgggng attattgcgt caacngcacn cccggcggan tgcgtgcata ttgccctgac     720
gggttttctt tccgggcgca tcgatttggt gatttccggc atcaacgccg gggcgaacct     780
gggcgatgat gtgctatatt ccggcacggt cgcggcagca tttgaagggc gtcatctggg     840
cttgccgtct attgcggtat cgctcgatgg tcgtcaacat tttgaaacgg cggcgcgcgt     900
ggtatgcgat ttggtgccga aattacacgc ccaattatta ggcaaacacg aaattctgaa     960
tattaacgtg cccgatgtgc cttacgaaga actgaaaggc attaaagtgt gccatttggg    1020
ctaccgttct tccgcttctg aagtgattaa acagcaaagc ccgcgtggcg aagacatgta    1080
ttggatc                                                             1087

<210> SEQ ID NO 6
<211> LENGTH: 681
<212> TYPE: DNA
<213> ORGANISM: Actinobacillus actinomycetemcomitans
<220> FEATURE:
<221> NAME/KEY: misc_feature
<222> LOCATION: (609)..(609)
<223> OTHER INFORMATION: N stands for any nucleotide
<220> FEATURE:
<221> NAME/KEY: misc_feature
<222> LOCATION: (614)..(614)
<223> OTHER INFORMATION: N stands for any nucleotide
<220> FEATURE:
<221> NAME/KEY: misc_feature
<222> LOCATION: (651)..(651)
<223> OTHER INFORMATION: N stands for any nucleotide
<220> FEATURE:
<221> NAME/KEY: misc_feature
<222> LOCATION: (665)..(665)
<223> OTHER INFORMATION: N stands for any nucleotide

<400> SEQUENCE: 6
gatctgccgt tggcgaaccc ttacgaaatg ctgatcctcg cgtccatcgt ggaaaaagaa      60
accggcattg ctgcagaacg cccacaagtg gcgtcggtat tcattaatcg gttaaaagcc     120
```

```
aaaatgaagc tgcaaaccga tccgaccgtc atttacggca tgggcgacga ctacaacggc      180
aatattcgca aaaagatttt ggaaacgcca acgccttata cacctatgt gattgacggc       240 ttgccgccga caccgattgc gatgccgagt gaagaggcgt tacaggcggt ggcacatccg      300
gcgcaaacgg cgttttatta tttcgtggca gacggcacgg ggggacacaa attcagtcgt     360
aatttaaacg aacataacaa agcggtgcag caatatttgc gctggtaccg cgaacaaaac     420
ggaaaataat atggtaggca aatttattgt cattgaaggc ttggaaggcg caggcaaaag      480
caccgctcat caatgcgttg tggatacgtt aaaaacgtta ggtgttgggg aagtcatctc      540
tacccgcgag ccgggcggca cacccgttgg cggaaaagct acgccatctc attaaacatg      600
aaaaccaana gccngtgacc cgataaagcg gaattactca tgctgtatgc ngccgcctgc      660
aattngtggg aaaatgtgat c                                                681
```

```
<210> SEQ ID NO 7
<211> LENGTH: 822
<212> TYPE: DNA
<213> ORGANISM: Actinobacillus actinomycetemcomitans
<220> FEATURE:
<221> NAME/KEY: misc_feature
<222> LOCATION: (532)..(532)
<223> OTHER INFORMATION: N stands for any nucleotide.
<220> FEATURE:
<221> NAME/KEY: misc_feature
<222> LOCATION: (630)..(630)
<223> OTHER INFORMATION: N stands for any nucleotide.
<220> FEATURE:
<221> NAME/KEY: misc_feature
<222> LOCATION: (696)..(696)
<223> OTHER INFORMATION: N stands for any nucleotide.
<220> FEATURE:
<221> NAME/KEY: misc_feature
<222> LOCATION: (710)..(710)
<223> OTHER INFORMATION: N stands for any nucleotide.
<220> FEATURE:
<221> NAME/KEY: misc_feature
<222> LOCATION: (722)..(722)
<223> OTHER INFORMATION: N stands for any nucleotide.
<220> FEATURE:
<221> NAME/KEY: misc_feature
<222> LOCATION: (725)..(725)
<223> OTHER INFORMATION: N stands for any nucleotide.

<400> SEQUENCE: 7
```

```
gatcgataaa aatcagcaag gcaaccactc ttaacaagaa ttgccatacc gtccaatatc      60
gtcgccaata ctgaatcgcg tagagcatgg ctaacgcaat catagcgcgt aaagtcggaa     120
tagcaagccc cgccagttgg ctgtataaca acgcaaaaat gaatccgcac agaatcggaa     180
atgtcgggct gatgtaacgc gtcggcaagg caaattgcag tagacgcgcc aaggtaaaac    240
ccagcatcat cgccagtccg atatgcagcc ctgaaatggc aattaaatgc gccgtatttg     300
ttttttgata aatttgccaa gttttttggt ctaagcggaa acgttcgcca aaaccgagtg    360
ccagcaacaa gccttgtcgg ggtaaattct ccgtttgttg taaggcttga ttgagagcgg     420
tttggcgtaa cgaaaaaacg ttttccaatt tgaccgcact tttaatctct gcccaagcgg     480
tgatgtgctt gccgaaatac catggctggc ggtcaaaacc gtcaaaattc angcgggaag    540
aaagcgctcg caagcgtaaa ttgcctgcgt aacgttcgcc cggggttgac tggttgcttg     600
agtttccatt gcgcgtaaat acgttgttcn gggaagattt tcggcgaagt tttgcgcccg    660
aataacccag gggttggata atgctgctga tgccanaaat ttccttgacn ggtaaatttc     720
cnggnggaac gggttttcgg cggcagattg gcaagattat ccgcctgggt cagtatggaa     780
attgccgatt ggtggacgta agcggactga atcatcaaga tc                      822
```

<210> SEQ ID NO 8
<211> LENGTH: 949
<212> TYPE: DNA
<213> ORGANISM: Actinobacillus actinomycetemcomitans
<220> FEATURE:
<221> NAME/KEY: misc_feature
<222> LOCATION: (538)..(538)
<223> OTHER INFORMATION: N stands for any nucleotide.

<400> SEQUENCE: 8

```
gatcaggttg ccgtaaccgc gtaaggcgtt acccgcgtaa accactcgac ctgcggcggc    60
ggcattgact gcttgtctgc gagaaccact gatgtcgatg cctttgttac cgccgtcggc   120
gttagagaaa ccttgaatca cattgccgtt ggtcggccag cgccatgcca cgttggatac   180
tgccggtgcg gtgcccgctt gggttatcgg ctgattggtt gccggtgcag cagtacctac   240
gccggcttta atcgggccgg taatcgtgcc gtcggaacca tattgtgtgc cgtttgcgcc   300
cggggtgtaa gttacggtcg gttcaccacc ttgcgtagcc ggttgggtga ccgtcggttg   360
catttgcggt gcagctttcg tttgcaccgt aaccgttgtg ccgcggctca cctttaaggt   420
ttgtccgacg cttaagctgt aaggttcgga catattattc aacgccgcca attctttcac   480
atccaaacca gaaatgtagg cgataaggaa catggtgtca cctttgcgta cggtatangt   540
ttcacctttg tagaaacctt tgttgatttg gctgtaatcc ggtgcgttag tggtcgggtt   600
acctggaatg gtgaaatctt gggatgcctg ttgcgggtga attttccccg gcaggttggg   660
tttgcttaac ccggttgtgc tttgcaatgc aaactgttga tacatcggtt gaaaaatcgg   720
ctgcggagta gattgtgcgc cggtcgcctg tagattgttc gactgggcaa tcggaccgtt   780
catcgaagcg ggtacattgc cttgttggat ttgcggttcc catgtgctat tgccgccatc   840
ggttgaaccg tccaccggtt gcatgagtcc cggggataag gtaccgtcgg cgttttccac   900
cggtgccggt gtattcgaag tacaggccgc taacacggca atgctgatc                949
```

<210> SEQ ID NO 9
<211> LENGTH: 277
<212> TYPE: DNA
<213> ORGANISM: Actinobacillus actinomycetemcomitans

<400> SEQUENCE: 9

```
agagaaaaaa ccggaagccg caccggcaga caaaccggcg gcagaagccc cggcaacaat    60
caaagtgggc gtgatggcag gaccggaaca ccaagtggct gaaatcgcag cgaaagtggc   120
aaaagaaaaa tacaacttag acgtagaata cgttttattc atgactacgc cttgccaaac   180
actgcagtgt ctaaaggtga tttagacgtt aacgcaatgc aacataaacc gtatttagac   240
aaagattccc aagcgaaagg attgaacaac ttagtga                             277
```

<210> SEQ ID NO 10
<211> LENGTH: 259
<212> TYPE: DNA
<213> ORGANISM: Actinobacillus actinomycetemcomitans

<400> SEQUENCE: 10

```
gatcaaactg gtggcgcaag ggcagcgcgt agcaaattta cccgatattt tggtctatgc    60
gcgcgtcggc aacggcatgg tagggcgacg ccgtggttta aaccaagcca agcggaatg    120
gcgcttattt aagctaaaac accatcttgg cattcaggga ttttatccg ggctattcac   180
ttttgtcctg cgttccggtg ccagattatt gccgacatca ttactgaaaa acatctatca   240
aaccttttta agaaaataa                                                 259
```

<210> SEQ ID NO 11
<211> LENGTH: 459
<212> TYPE: DNA
<213> ORGANISM: Actinobacillus actinomycetemcomitans

<400> SEQUENCE: 11

| | | | | | | |
|---|---|---|---|---|---|---|
| gatcgcaaca | agcgcagttt | ctatatttcc | gccgcccgca | gtgagatttt | caatttaatc | 60 |
| gttgccaaac | gtattgaact | cagtctggcg | cagcaggtct | taaatggaga | cgttttgcaa | 120 |
| ctgaacggtt | cgcacagttg | gtttgtggcg | gacgcatcgg | aagatttgac | gcaactgcaa | 180 |
| caacgcttgg | cacaacggga | tattttgctt | accgcaccgc | ttatcggcga | agaggacaaa | 240 |
| agtgcggtgg | attttgagaa | tgaaattttt | gtcgcgcacc | aagccttgtt | ccatttgatg | 300 |
| cggcaagaac | gcgtgaaagc | cgcccgccgt | ccgattttaa | tgcaggcgca | acagtttcaa | 360 |
| tggcaatttg | aaccgaacgg | tttgcgcctt | aaattttatt | tgccggcagg | cagttacgcc | 420 |
| acggcgttgg | tacgcgagct | ggtgaatgtt | gaaaactga | | | 459 |

<210> SEQ ID NO 12
<211> LENGTH: 596
<212> TYPE: DNA
<213> ORGANISM: Actinobacillus actinomycetemcomitans
<220> FEATURE:
<221> NAME/KEY: misc_feature
<222> LOCATION: (131)..(131)
<223> OTHER INFORMATION: N stands for any nucleotide.
<220> FEATURE:
<221> NAME/KEY: misc_feature
<222> LOCATION: (151)..(151)
<223> OTHER INFORMATION: N stands for any nucleotide.
<220> FEATURE:
<221> NAME/KEY: misc_feature
<222> LOCATION: (170)..(170)
<223> OTHER INFORMATION: N stands for any nucleotide.
<220> FEATURE:
<221> NAME/KEY: misc_feature
<222> LOCATION: (178)..(178)
<223> OTHER INFORMATION: N stands for any nucleotide.
<220> FEATURE:
<221> NAME/KEY: misc_feature
<222> LOCATION: (194)..(194)
<223> OTHER INFORMATION: N stands for any nucleotide.
<220> FEATURE:
<221> NAME/KEY: misc_feature
<222> LOCATION: (199)..(199)
<223> OTHER INFORMATION: N stands for any nucleotide.
<220> FEATURE:
<221> NAME/KEY: misc_feature
<222> LOCATION: (209)..(209)
<223> OTHER INFORMATION: N stands for any nucleotide.

<400> SEQUENCE: 12

| | | | | | | |
|---|---|---|---|---|---|---|
| atgaatattt | tattaagtaa | cgatgacggc | attcacgcgc | cgggcattcg | tgtgatggca | 60 |
| gaacattgcg | taagattgcc | aatgtgacca | tcgtcgcgcc | ggacagcaac | cgcaagcgcc | 120 |
| gccttcagtt | ncttaacctt | ggtgaagccg | ntgtattccg | ttcatttggn | aaagcggnga | 180 |
| ttattgcgtc | aacngcacnc | ccggcggant | gcgtgcatat | tgccctgacg | ggttttctt | 240 |
| ccgggcgcat | cgatttggtg | atttccggca | tcaacgccgg | ggcgaacctg | ggcgatgatg | 300 |
| tgctatattc | cggcacggtc | gcggcagcat | ttgaagggcg | tcatctgggc | ttgccgtcta | 360 |
| ttgcggtatc | gctcgatggt | cgtcaacatt | ttgaaacggc | ggcgcgcgtg | gtatgcgatt | 420 |
| tggtgccgaa | attacacgcc | caattattag | gcaaacacga | aattctgaat | attaacgtgc | 480 |
| ccgatgtgcc | ttacgaagaa | ctgaaaggca | ttaaagtgtg | ccatttgggc | taccgttctt | 540 |
| ccgcttctga | agtgattaaa | cagcaaagcc | cgcgtggcga | agacatgtat | tggatc | 596 |

<210> SEQ ID NO 13
<211> LENGTH: 429
<212> TYPE: DNA
<213> ORGANISM: Actinobacillus actinomycetemcomitans

<400> SEQUENCE: 13

```
gatctgccgt tggcgaaccc ttacgaaatg ctgatcctcg cgtccatcgt ggaaaaagaa    60
accggcattg ctgcagaacg cccacaagtg gcgtcggtat tcattaatcg gttaaaagcc   120
aaaatgaagc tgcaaaccga tccgaccgtc atttacggca tgggcgacga ctacaacggc   180
aatattcgca aaaagattt ggaaacgcca acgccttata cacctatgt gattgacggc    240
ttgccgccga caccgattgc gatgccgagt gaagaggcgt tacaggcggt ggcacatccg   300
gcgcaaacgg cgttttatta tttcgtggca gacggcacgg ggggacacaa attcagtcgt   360
aatttaaacg aacataacaa agcggtgcag caatatttgc gctggtaccg cgaacaaaac   420
ggaaaataa                                                           429
```

<210> SEQ ID NO 14
<211> LENGTH: 162
<212> TYPE: DNA
<213> ORGANISM: Actinobacillus actinomycetemcomitans

<400> SEQUENCE: 14

```
atggtaggca aatttattgt cattgaaggc ttggaaggcg caggcaaaag caccgctcat    60
caatgcgttg tggatacgtt aaaaacgtta ggtgttgggg aagtcatctc tacccgcgag   120
ccgggcggca cacccgttgg cggaaaagct acgccatctc at                      162
```

<210> SEQ ID NO 15
<211> LENGTH: 67
<212> TYPE: PRT
<213> ORGANISM: Actinobacillus actinomycetemcomitans

<400> SEQUENCE: 15

Glu Lys Lys Pro Glu Ala Ala Pro Ala Asp Lys Pro Ala Ala Glu Ala
1               5                  10                  15

Pro Ala Thr Ile Lys Val Gly Val Met Ala Gly Pro Glu His Gln Val
            20                  25                  30

Ala Glu Ile Ala Ala Lys Val Ala Lys Glu Lys Tyr Asn Leu Asp Val
        35                  40                  45

Glu Tyr Val Leu Phe Met Thr Thr Pro Cys Gln Thr Leu Gln Cys Leu
    50                  55                  60

Lys Val Ile
65

<210> SEQ ID NO 16
<211> LENGTH: 85
<212> TYPE: PRT
<213> ORGANISM: Actinobacillus actinomycetemcomitans

<400> SEQUENCE: 16

Ile Lys Leu Val Ala Gln Gly Gln Arg Val Ala Asn Leu Pro Asp Ile
1               5                  10                  15

Leu Val Tyr Ala Arg Val Gly Asn Gly Met Val Gly Arg Arg Gly
            20                  25                  30

Leu Asn Gln Ala Lys Ala Glu Trp Arg Leu Phe Lys Leu Lys His His
        35                  40                  45

Leu Gly Ile Gln Gly Phe Leu Ser Gly Leu Phe Thr Phe Val Leu Arg 50                  55                  60
Ser Gly Ala Arg Leu Leu Pro Thr Ser Leu Leu Lys Asn Ile Tyr Gln
 65                  70                  75                  80

Thr Phe Leu Arg Lys
                85

<210> SEQ ID NO 17
<211> LENGTH: 152
<212> TYPE: PRT
<213> ORGANISM: Actinobacillus actinomycetemcomitans

<400> SEQUENCE: 17

Asp Arg Asn Lys Arg Ser Phe Tyr Ile Ser Ala Ala Arg Ser Glu Ile
 1               5                  10                  15

Phe Asn Leu Ile Val Ala Lys Arg Ile Glu Leu Ser Leu Ala Gln Gln
                20                  25                  30

Val Leu Asn Gly Asp Val Leu Gln Leu Asn Gly Ser His Ser Trp Phe
            35                  40                  45

Val Ala Asp Ala Ser Glu Asp Leu Thr Gln Leu Gln Gln Arg Leu Ala
 50                  55                  60

Gln Arg Asp Ile Leu Leu Thr Ala Pro Leu Ile Gly Glu Glu Asp Lys
 65                  70                  75                  80

Ser Ala Val Asp Phe Glu Asn Glu Ile Phe Val Ala His Gln Ala Leu
                85                  90                  95

Phe His Leu Met Arg Gln Glu Arg Val Lys Ala Ala Arg Arg Pro Ile
            100                 105                 110

Leu Met Gln Ala Gln Gln Phe Gln Trp Gln Phe Glu Pro Asn Gly Leu
        115                 120                 125

Arg Leu Lys Phe Tyr Leu Pro Ala Gly Ser Tyr Ala Thr Ala Leu Val
    130                 135                 140

Arg Glu Leu Val Asn Val Glu Asn
145                 150

<210> SEQ ID NO 18
<211> LENGTH: 208
<212> TYPE: PRT
<213> ORGANISM: Actinobacillus actinomycetemcomitans
<220> FEATURE:
<221> NAME/KEY: MISC_FEATURE
<222> LOCATION: (43)..(43)
<223> OTHER INFORMATION: Xaa stands for any amino acid.
<220> FEATURE:
<221> NAME/KEY: MISC_FEATURE
<222> LOCATION: (52)..(52)
<223> OTHER INFORMATION: Xaa stands for any amino acid.
<220> FEATURE:
<221> NAME/KEY: MISC_FEATURE
<222> LOCATION: (63)..(63)
<223> OTHER INFORMATION: Xaa stands for any amino acid.
<220> FEATURE:
<221> NAME/KEY: MISC_FEATURE
<222> LOCATION: (72)..(72)
<223> OTHER INFORMATION: Xaa stands for any amino acid.
<220> FEATURE:
<221> NAME/KEY: MISC_FEATURE
<222> LOCATION: (77)..(77)
<223> OTHER INFORMATION: Xaa stands for any amino acid.

<400> SEQUENCE: 18

Met Asn Ile Leu Leu Ser Asn Asp Asp Gly Ile His Ala Pro Gly Ile
 1               5                  10                  15

Arg Val Met Arg Thr Leu Arg Lys Ile Ala Asn Val Thr Ile Val Ala
                20                  25                  30

```
Pro Asp Ser Asn Arg Lys Arg Arg Leu Gln Xaa Ala Ala Leu Asn Leu
            35                  40                  45

Gly Glu Ala Xaa Ala Ala Val Phe Arg Ser Phe Gly Lys Ala Xaa Ala
        50                  55                  60

Ala Ile Ile Ala Ser Thr Ala Xaa Ala Ala Pro Ala Xaa Ala Ala Cys
 65                  70                  75                  80

Val His Ile Ala Leu Thr Gly Phe Leu Ser Gly Arg Ile Asp Leu Val
                85                  90                  95

Ile Ser Gly Ile Asn Ala Gly Ala Asn Leu Gly Asp Asp Val Leu Tyr
                100                 105                 110

Ser Gly Thr Val Ala Ala Ala Phe Glu Gly Arg His Leu Gly Leu Pro
            115                 120                 125

Ser Ile Ala Val Ser Leu Asp Gly Arg Gln His Phe Glu Thr Ala Ala
        130                 135                 140

Arg Val Val Cys Asp Leu Val Pro Lys Leu His Ala Gln Leu Leu Gly
145                 150                 155                 160

Lys His Glu Ile Leu Asn Ile Asn Val Pro Asp Val Pro Tyr Glu Glu
                165                 170                 175

Leu Lys Gly Ile Lys Val Cys His Leu Gly Tyr Arg Ser Ser Ala Ser
            180                 185                 190

Glu Val Ile Lys Gln Gln Ser Pro Arg Gly Glu Asp Met Tyr Trp Ile
        195                 200                 205

<210> SEQ ID NO 19
<211> LENGTH: 142
<212> TYPE: PRT
<213> ORGANISM: Actinobacillus actinomycetemcomitans

<400> SEQUENCE: 19

Asp Leu Pro Leu Ala Asn Pro Tyr Glu Met Leu Ile Leu Ala Ser Ile
1               5                   10                  15

Val Glu Lys Glu Thr Gly Ile Ala Ala Glu Arg Pro Gln Val Ala Ser
            20                  25                  30

Val Phe Ile Asn Arg Leu Lys Ala Lys Met Lys Leu Gln Thr Asp Pro
        35                  40                  45

Thr Val Ile Tyr Gly Met Gly Asp Asp Tyr Asn Gly Asn Ile Arg Lys
 50                  55                  60

Lys Asp Leu Glu Thr Pro Thr Pro Tyr Asn Thr Tyr Val Ile Asp Gly
65                  70                  75                  80

Leu Pro Pro Thr Pro Ile Ala Met Pro Ser Glu Glu Ala Leu Gln Ala
                85                  90                  95

Val Ala His Pro Ala Gln Thr Ala Phe Tyr Tyr Phe Val Ala Asp Gly
            100                 105                 110

Thr Gly Gly His Lys Phe Ser Arg Asn Leu Asn Glu His Asn Lys Ala
        115                 120                 125

Val Gln Gln Tyr Leu Arg Trp Tyr Arg Glu Gln Asn Gly Lys
    130                 135                 140

<210> SEQ ID NO 20
<211> LENGTH: 54
<212> TYPE: PRT
<213> ORGANISM: Actinobacillus actinomycetemcomitans

<400> SEQUENCE: 20

Met Val Gly Lys Phe Ile Val Ile Glu Gly Leu Glu Gly Ala Gly Lys
1               5                   10                  15

Ser Thr Ala His Gln Cys Val Val Asp Thr Leu Lys Thr Leu Gly Val
```

-continued

```
            20                  25                  30
Gly Glu Val Ile Ser Thr Arg Glu Pro Gly Gly Thr Pro Val Gly Gly
        35                  40                  45

Lys Ala Thr Pro Ser His
    50
```